(12) United States Patent  (10) Patent No.: US 7,914,556 B2
Broman et al.  (45) Date of Patent: Mar. 29, 2011

(54) ARTHROPLASTY REVISION SYSTEM AND METHOD

(75) Inventors: Richard Broman, Kirkland, WA (US); Thomas McLeer, Redmond, WA (US); Leonard Tokish, Jr., Issaquah, WA (US); Mark A. Reiley, Piedmont, CA (US); Sean S. Suh, Kirkland, WA (US)

(73) Assignee: Gmedelaware 2 LLC, Audubon, PA (US)

( * ) Notice: Subject to any disclaimer, the term of this patent is extended or adjusted under 35 U.S.C. 154(b) by 863 days.

(21) Appl. No.: 11/642,417

(22) Filed: Dec. 20, 2006

(65) Prior Publication Data

US 2007/0276374 A1   Nov. 29, 2007

Related U.S. Application Data

(63) Continuation-in-part of application No. 11/206,676, filed on Aug. 17, 2005, which is a continuation-in-part of application No. 11/071,541, filed on Mar. 2, 2005.

(60) Provisional application No. 60/847,013, filed on Sep. 25, 2006, provisional application No. 60/752,277, filed on Dec. 20, 2005.

(51) Int. Cl.
 *A61B 17/70* (2006.01)
(52) U.S. Cl. ........................................................ 606/246
(58) Field of Classification Search .................. 606/264, 606/301, 305, 247, 246, 308, 304, 250, 279
 See application file for complete search history.

(56) References Cited

U.S. PATENT DOCUMENTS

| 1,308,451 | A | 7/1919 | Schachat |
| 2,502,902 | A | 4/1950 | Tofflemire |
| 2,930,133 | A | 3/1960 | Thompson |
| 2,959,861 | A | 11/1960 | Stromquist |
| 3,596,656 | A | 8/1971 | Kaute |
| 3,710,789 | A | 1/1973 | Ersek |

(Continued)

FOREIGN PATENT DOCUMENTS

DE    10135771 A1    7/2001

(Continued)

OTHER PUBLICATIONS

Ochoa et al.; U.S. Appl. No. 12/377,546 entitled "Spinal implant," filed Feb. 13, 2009.

(Continued)

*Primary Examiner* — Pedro Philogene

(57) ABSTRACT

The invention provides a method of revising an implanted spinal device, such as an implanted arthroplasty device having a cephalad component fixed to a first vertebra and a caudal component fixed to a second vertebra inferior to the first vertebra. The method includes the following steps: removing a portion of a previously implanted spinal arthroplasty device; and attaching a revision component to a remaining portion of the previously implanted spinal arthroplasty device to alter a biomechanical characteristic of the implanted arthroplasty device. Another aspect of the invention provides a method of limiting motion between adjacent vertebrae including the steps of accessing an implanted spinal arthroplasty device comprising a cephalad component fixed to a first vertebra and a caudal component fixed to a second vertebra inferior to the first vertebra, the cephalad and caudal components having a range of motion between them, and attaching a revision component to the cephalad and caudal components to reduce the range of motion. The invention also includes revision devices for revising the biomechanics of implanted spinal arthroplasty devices.

39 Claims, 13 Drawing Sheets

U.S. PATENT DOCUMENTS

| | | |
|---|---|---|
| 3,726,279 A | 4/1973 | Barefoot et al. |
| 3,867,728 A | 2/1975 | Stubstad et al. |
| 3,875,595 A | 4/1975 | Froning |
| 3,941,127 A | 3/1976 | Froning |
| 4,040,130 A | 8/1977 | Laure |
| 4,123,848 A | 11/1978 | Emmerich et al. |
| 4,156,296 A | 5/1979 | Johnson et al. |
| 4,210,317 A | 7/1980 | Spann et al. |
| 4,231,121 A | 11/1980 | Lewis |
| 4,271,836 A | 6/1981 | Bacal et al. |
| 4,349,921 A | 9/1982 | Kuntz |
| 4,394,370 A | 7/1983 | Jefferies |
| 4,472,840 A | 9/1984 | Jefferies |
| 4,502,161 A | 3/1985 | Wall |
| 4,554,914 A | 11/1985 | Kapp et al. |
| 4,611,581 A | 9/1986 | Steffee |
| 4,633,722 A | 1/1987 | Beardmore et al. |
| 4,693,722 A | 9/1987 | Wall |
| 4,697,582 A | 10/1987 | William |
| 4,710,075 A | 12/1987 | Davison |
| 4,759,769 A | 7/1988 | Hedman et al. |
| 4,772,287 A | 9/1988 | Ray et al. |
| 4,778,472 A | 10/1988 | Homsy et al. |
| 4,795,469 A | 1/1989 | Oh |
| 4,805,602 A | 2/1989 | Puno et al. |
| 4,863,477 A | 9/1989 | Monson |
| 4,904,260 A | 2/1990 | Ray et al. |
| 4,911,718 A | 3/1990 | Lee et al. |
| 4,917,701 A | 4/1990 | Morgan |
| 4,932,975 A | 6/1990 | Main et al. |
| 4,950,270 A | 8/1990 | Bowman et al. |
| 4,955,916 A | 9/1990 | Carignan et al. |
| 4,957,495 A | 9/1990 | Kluger |
| 4,987,904 A | 1/1991 | Wilson |
| 5,000,165 A | 3/1991 | Watanabe |
| 5,015,255 A | 5/1991 | Kuslich |
| 5,019,081 A | 5/1991 | Watanabe |
| 5,047,055 A | 9/1991 | Bao et al. |
| 5,062,845 A | 11/1991 | Kuslich et al. |
| 5,070,623 A | 12/1991 | Barnes |
| 5,071,437 A | 12/1991 | Steffee |
| 5,092,866 A | 3/1992 | Breard et al. |
| 5,098,434 A | 3/1992 | Serbousek |
| 5,108,399 A | 4/1992 | Eitenmuller et al. |
| 5,129,900 A | 7/1992 | Asher et al. |
| 5,147,404 A | 9/1992 | Downey |
| 5,171,280 A | 12/1992 | Baumgartner |
| 5,192,326 A | 3/1993 | Bao et al. |
| 5,258,031 A | 11/1993 | Salib et al. |
| 5,261,910 A | 11/1993 | Warden et al. |
| 5,284,655 A | 2/1994 | Bogdansky et al. |
| 5,300,073 A | 4/1994 | Ray et al. |
| 5,303,480 A | 4/1994 | Chek |
| 5,306,308 A | 4/1994 | Gross et al. |
| 5,306,309 A | 4/1994 | Wagner et al. |
| 5,312,409 A | 5/1994 | McLaughlin et al. |
| 5,314,429 A | 5/1994 | Goble |
| 5,314,476 A | 5/1994 | Prewett et al. |
| 5,314,486 A | 5/1994 | Zang et al. |
| 5,314,489 A | 5/1994 | Hoffman et al. |
| 5,314,492 A | 5/1994 | Hamilton et al. |
| 5,329,933 A | 7/1994 | Graf |
| 5,334,203 A | 8/1994 | Wagner |
| 5,348,026 A | 9/1994 | Davidson |
| 5,350,380 A | 9/1994 | Goble et al. |
| 5,360,448 A | 11/1994 | Thramann |
| 5,366,455 A | 11/1994 | Dove et al. |
| 5,370,697 A | 12/1994 | Baumgartner |
| 5,401,269 A | 3/1995 | Buttner-Janz et al. |
| 5,405,390 A | 4/1995 | O'Leary et al. |
| 5,413,576 A | 5/1995 | Rivard |
| 5,415,659 A | 5/1995 | Lee et al. |
| 5,415,661 A | 5/1995 | Holmes |
| 5,425,773 A | 6/1995 | Boyd et al. |
| 5,437,669 A | 8/1995 | Yuan et al. |
| 5,437,672 A | 8/1995 | Alleyne |
| 5,443,483 A | 8/1995 | Kirsch |
| 5,445,639 A | 8/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,470,333 A | 11/1995 | Ray |
| 5,474,551 A | 12/1995 | Finn et al. |
| 5,474,555 A | 12/1995 | Puno et al. |
| 5,491,882 A | 2/1996 | Walston et al. |
| 5,496,318 A | 3/1996 | Howland et al. |
| 5,501,684 A | 3/1996 | Schlapfer et al. |
| 5,507,745 A | 4/1996 | Logroscino et al. |
| 5,507,823 A | 4/1996 | Walston et al. |
| 5,510,396 A | 4/1996 | Prewett et al. |
| 5,514,180 A | 5/1996 | Heggeness et al. |
| 5,527,312 A | 6/1996 | Ray |
| 5,534,028 A | 7/1996 | Bao et al. |
| 5,534,030 A | 7/1996 | Navarro et al. |
| 5,545,229 A | 8/1996 | Parsons et al. |
| 5,556,431 A | 9/1996 | Buttner-Janz |
| 5,562,738 A | 10/1996 | Boyd et al. |
| 5,569,247 A | 10/1996 | Morrison |
| 5,571,189 A | 11/1996 | Kuslich |
| 5,571,191 A | 11/1996 | Fitz |
| 5,575,792 A | 11/1996 | Errico et al. |
| 5,577,995 A | 11/1996 | Walker et al. |
| 5,587,695 A | 12/1996 | Warmerdam |
| 5,599,311 A | 2/1997 | Raulerson |
| 5,603,713 A | 2/1997 | Aust et al. |
| 5,609,641 A | 3/1997 | Johnson et al. |
| 5,643,263 A | 7/1997 | Simonson |
| 5,645,597 A | 7/1997 | Krapiva |
| 5,645,599 A | 7/1997 | Samani |
| 5,649,930 A | 7/1997 | Kertzner |
| 5,653,762 A | 8/1997 | Pisharodi |
| 5,658,338 A | 8/1997 | Tullos et al. |
| 5,662,651 A | 9/1997 | Tornier et al. |
| 5,672,175 A | 9/1997 | Martin |
| 5,674,295 A | 10/1997 | Ray et al. |
| 5,674,296 A | 10/1997 | Bryan et al. |
| 5,676,701 A | 10/1997 | Yuan et al. |
| 5,678,317 A | 10/1997 | Stefanakos |
| 5,683,391 A | 11/1997 | Boyd |
| 5,683,392 A | 11/1997 | Richelsoph et al. |
| 5,683,464 A | 11/1997 | Wagner et al. |
| 5,683,466 A | 11/1997 | Vitale |
| 5,688,274 A | 11/1997 | Errico et al. |
| 5,690,630 A | 11/1997 | Errico et al. |
| 5,700,268 A | 12/1997 | Bertin |
| 5,702,450 A | 12/1997 | Bisserie |
| 5,704,941 A | 1/1998 | Jacober et al. |
| 5,716,415 A | 2/1998 | Steffee |
| 5,725,527 A | 3/1998 | Biedermann et al. |
| 5,733,284 A | 3/1998 | Martin |
| 5,738,585 A | 4/1998 | Hoyt, III et al. |
| 5,741,255 A | 4/1998 | Krag et al. |
| 5,741,261 A | 4/1998 | Moskovitz et al. |
| 5,766,253 A | 6/1998 | Brosnahan, III |
| 5,776,135 A | 7/1998 | Errico et al. |
| 5,782,833 A | 7/1998 | Haider |
| 5,797,911 A | 8/1998 | Sherman et al. |
| 5,800,433 A | 9/1998 | Benzel et al. |
| 5,824,093 A | 10/1998 | Ray et al. |
| 5,824,094 A | 10/1998 | Serhan et al. |
| 5,827,289 A | 10/1998 | Reiley et al. |
| 5,836,948 A | 11/1998 | Zucherman et al. |
| 5,860,977 A | 1/1999 | Zucherman et al. |
| 5,863,293 A | 1/1999 | Richelsoph |
| 5,865,846 A | 2/1999 | Bryan et al. |
| 5,866,113 A | 2/1999 | Hendriks et al. |
| 5,868,745 A | 2/1999 | Alleyne |
| 5,879,350 A | 3/1999 | Sherman et al. |
| 5,879,396 A | 3/1999 | Walston et al. |
| 5,885,285 A | 3/1999 | Simonson |
| 5,885,286 A | 3/1999 | Sherman et al. |
| 5,891,145 A | 4/1999 | Morrison et al. |
| 5,893,889 A | 4/1999 | Harrington |
| RE36,221 E | 6/1999 | Breard et al. |
| 5,947,893 A | 9/1999 | Agrawal et al. |
| 5,947,965 A | 9/1999 | Bryan |
| 5,964,760 A | 10/1999 | Richelsoph |

| | | | | | | |
|---|---|---|---|---|---|---|
| 5,984,926 | A | 11/1999 | Jones | 6,736,815 B2 | 5/2004 | Ginn |
| 6,001,130 | A | 12/1999 | Bryan et al. | 6,749,361 B2 | 6/2004 | Hermann et al. |
| 6,004,353 | A | 12/1999 | Masini | 6,749,613 B1 * | 6/2004 | Conchy et al. ............... 606/57 |
| 6,010,503 | A | 1/2000 | Richelsoph et al. | 6,761,698 B2 | 7/2004 | Shibata et al. |
| 6,014,588 | A | 1/2000 | Fitz | 6,761,720 B1 | 7/2004 | Senegas |
| 6,019,759 | A | 2/2000 | Rogozinski | 6,770,095 B2 | 8/2004 | Grinberg et al. |
| 6,019,792 | A | 2/2000 | Cauthen | 6,783,527 B2 | 8/2004 | Drewry et al. |
| 6,022,350 | A | 2/2000 | Ganem | 6,790,233 B2 | 9/2004 | Brodke et al. |
| 6,039,763 | A | 3/2000 | Shelokov | 6,793,678 B2 | 9/2004 | Hawkins |
| 6,048,342 | A | 4/2000 | Zucherman et al. | 6,802,844 B2 | 10/2004 | Ferree |
| 6,050,997 | A | 4/2000 | Mullane | 6,811,567 B2 | 11/2004 | Reiley |
| 6,053,917 | A | 4/2000 | Sherman et al. | 6,902,567 B2 | 6/2005 | Del Medico |
| 6,063,121 | A | 5/2000 | Xavier et al. | 6,902,580 B2 | 6/2005 | Fallin et al. |
| 6,066,325 | A | 5/2000 | Wallace et al. | 6,908,465 B2 | 6/2005 | von Hoffmann et al. |
| 6,068,630 | A | 5/2000 | Zucherman et al. | 6,916,319 B2 * | 7/2005 | Munting ................ 606/278 |
| RE36,758 | E | 6/2000 | Fitz | 6,949,123 B2 | 9/2005 | Reiley |
| 6,074,391 | A | 6/2000 | Metz-Stavenhagen et al. | 6,974,478 B2 | 12/2005 | Reiley et al. |
| 6,077,262 | A | 6/2000 | Schläpfer et al. | 6,979,299 B2 | 12/2005 | Peabody et al. |
| 6,080,157 | A | 6/2000 | Cathro et al. | 7,008,423 B2 * | 3/2006 | Assaker et al. ............. 606/250 |
| 6,086,590 | A | 7/2000 | Margulies et al. | 7,011,658 B2 | 3/2006 | Young |
| 6,090,111 | A | 7/2000 | Nichols | 7,044,969 B2 | 5/2006 | Errico et al. |
| 6,113,600 | A | 9/2000 | Drummond et al. | 7,051,451 B2 | 5/2006 | Augostino et al. |
| 6,113,637 | A | 9/2000 | Gill et al. | 7,220,262 B1 | 5/2007 | Hynes |
| 6,120,510 | A | 9/2000 | Albrektsson et al. | 7,294,127 B2 | 11/2007 | Leung et al. |
| 6,132,430 | A | 10/2000 | Wagner | 7,302,288 B1 | 11/2007 | Schellenberg |
| 6,132,462 | A | 10/2000 | Li | 7,309,338 B2 | 12/2007 | Cragg |
| 6,132,464 | A | 10/2000 | Martin | 7,445,635 B2 | 11/2008 | Fallin et al. |
| 6,132,465 | A | 10/2000 | Ray et al. | 7,455,685 B2 | 11/2008 | Justis |
| 6,165,177 | A | 12/2000 | Wilson et al. | 7,547,324 B2 | 6/2009 | Cragg et al. |
| 6,190,388 | B1 | 2/2001 | Michelson et al. | 7,691,145 B2 * | 4/2010 | Reiley et al. ............... 623/17.11 |
| 6,193,724 | B1 | 2/2001 | Chan | 2001/0012938 A1 | 8/2001 | Zucherman et al. |
| 6,193,758 | B1 | 2/2001 | Huebner | 2001/0020170 A1 | 9/2001 | Zucherman et al. |
| 6,200,322 | B1 | 3/2001 | Branch et al. | 2002/0013585 A1 | 1/2002 | Gournay et al. |
| 6,214,012 | B1 | 4/2001 | Karpman et al. | 2002/0013588 A1 | 1/2002 | Landry et al. |
| 6,224,602 | B1 | 5/2001 | Hayes | 2002/0029039 A1 | 3/2002 | Zucherman et al. |
| 6,231,575 | B1 | 5/2001 | Krag | 2002/0042613 A1 | 4/2002 | Mata |
| 6,248,105 | B1 | 6/2001 | Schläpfer et al. | 2002/0049446 A1 | 4/2002 | Harkey, III et al. |
| 6,280,443 | B1 | 8/2001 | Gu et al. | 2002/0052603 A1 | 5/2002 | Nickols et al. |
| 6,290,703 | B1 | 9/2001 | Ganem | 2002/0065557 A1 | 5/2002 | Goble et al. |
| 6,293,949 | B1 | 9/2001 | Justis et al. | 2002/0068975 A1 | 6/2002 | Teitelbaum et al. |
| 6,302,890 | B1 | 10/2001 | Leone, Jr. | 2002/0082601 A1 | 6/2002 | Toyoma et al. |
| 6,309,391 | B1 | 10/2001 | Crandall et al. | 2002/0120272 A1 | 8/2002 | Yuan et al. |
| 6,312,431 | B1 | 11/2001 | Asfora | 2002/0123752 A1 | 9/2002 | Schultheiss et al. |
| 6,340,361 | B1 | 1/2002 | Kraus et al. | 2002/0123806 A1 | 9/2002 | Reiley |
| 6,340,477 | B1 | 1/2002 | Anderson | 2002/0151895 A1 | 10/2002 | Soboleski et al. |
| 6,342,054 | B1 | 1/2002 | Mata | 2003/0004572 A1 | 1/2003 | Goble et al. |
| 6,361,506 | B1 | 3/2002 | Saenger et al. | 2003/0028250 A1 | 2/2003 | Reiley et al. |
| 6,368,320 | B1 | 4/2002 | Le Couedic et al. | 2003/0040797 A1 | 2/2003 | Fallin et al. |
| 6,419,703 | B1 | 7/2002 | Fallin et al. | 2003/0055427 A1 | 3/2003 | Graf |
| 6,440,169 | B1 | 8/2002 | Elberg et al. | 2003/0069603 A1 | 4/2003 | Little et al. |
| 6,443,954 | B1 | 9/2002 | Bramlet et al. | 2003/0125740 A1 | 7/2003 | Khanna |
| 6,451,021 | B1 | 9/2002 | Ralph et al. | 2003/0181914 A1 | 9/2003 | Johnson et al. |
| 6,471,705 | B1 | 10/2002 | Biedermann et al. | 2003/0191532 A1 | 10/2003 | Goble et al. |
| 6,514,253 | B1 | 2/2003 | Yao | 2003/0195631 A1 | 10/2003 | Ferree |
| 6,520,963 | B1 | 2/2003 | McKinley | 2003/0204259 A1 | 10/2003 | Goble et al. |
| 6,524,315 | B1 | 2/2003 | Seivitelli et al. | 2003/0204261 A1 | 10/2003 | Eisermann et al. |
| 6,540,749 | B2 | 4/2003 | Schäfer et al. | 2003/0233148 A1 | 12/2003 | Ferree |
| 6,547,790 | B2 | 4/2003 | Harkey, III et al. | 2004/0006391 A1 | 1/2004 | Reiley |
| 6,554,843 | B1 | 4/2003 | Ou | 2004/0049205 A1 | 3/2004 | Lee et al. |
| 6,565,565 | B1 | 5/2003 | Yuan et al. | 2004/0049272 A1 | 3/2004 | Reiley |
| 6,565,572 | B2 | 5/2003 | Chappius | 2004/0049273 A1 | 3/2004 | Reiley |
| 6,565,605 | B2 | 5/2003 | Goble et al. | 2004/0049274 A1 | 3/2004 | Reiley |
| 6,572,617 | B1 | 6/2003 | Senegas | 2004/0049275 A1 | 3/2004 | Reiley |
| 6,579,319 | B2 | 6/2003 | Goble et al. | 2004/0049276 A1 | 3/2004 | Reiley |
| 6,585,740 | B2 | 7/2003 | Schlapfer et al. | 2004/0049277 A1 | 3/2004 | Reiley |
| 6,585,769 | B1 | 7/2003 | Muhanna et al. | 2004/0049278 A1 | 3/2004 | Reiley |
| 6,607,530 | B1 | 8/2003 | Carl et al. | 2004/0049281 A1 | 3/2004 | Reiley |
| 6,610,091 | B1 | 8/2003 | Reiley | 2004/0059429 A1 | 3/2004 | Amin et al. |
| 6,619,091 | B2 | 9/2003 | Heffe | 2004/0111154 A1 | 6/2004 | Reiley |
| 6,623,485 | B2 | 9/2003 | Doubler et al. | 2004/0116927 A1 | 6/2004 | Graf |
| 6,626,909 | B2 | 9/2003 | Chin | 2004/0127989 A1 | 7/2004 | Dooris et al. |
| 6,632,226 | B2 | 10/2003 | Chan | 2004/0143264 A1 | 7/2004 | McAfee |
| 6,638,281 | B2 | 10/2003 | Gorek | 2004/0204710 A1 | 10/2004 | Patel et al. |
| 6,645,214 | B2 | 11/2003 | Brown et al. | 2004/0204718 A1 | 10/2004 | Hoffman |
| 6,648,891 | B2 | 11/2003 | Kim | 2004/0230201 A1 | 11/2004 | Yuan et al. |
| 6,669,698 | B1 | 12/2003 | Tromanhauser et al. | 2004/0230304 A1 | 11/2004 | Yuan et al. |
| 6,669,729 | B2 | 12/2003 | Chin | 2004/0260305 A1 | 12/2004 | Gorensek et al. |
| 6,712,818 | B1 | 3/2004 | Michelson | 2004/0267279 A1 | 12/2004 | Casutt et al. |
| 6,712,849 | B2 | 3/2004 | Re et al. | 2005/0010291 A1 | 1/2005 | Stinson et al. |

| | | |
|---|---|---|
| 2005/0015146 A1 | 1/2005 | Louis et al. |
| 2005/0027359 A1 | 2/2005 | Mashburn |
| 2005/0027361 A1 | 2/2005 | Reiley |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0033439 A1 | 2/2005 | Gordon et al. |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0059972 A1 | 3/2005 | Biscup |
| 2005/0080428 A1 | 4/2005 | White |
| 2005/0080486 A1 | 4/2005 | Fallin et al. |
| 2005/0085912 A1 | 4/2005 | Arnin et al. |
| 2005/0101956 A1 | 5/2005 | Simonson |
| 2005/0102028 A1 | 5/2005 | Arnin et al. |
| 2005/0119748 A1 | 6/2005 | Reiley et al. |
| 2005/0131406 A1 | 6/2005 | Reiley et al. |
| 2005/0131409 A1 | 6/2005 | Chervitz et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0137705 A1 | 6/2005 | Reiley |
| 2005/0137706 A1 | 6/2005 | Reiley |
| 2005/0143818 A1 | 6/2005 | Yuan et al. |
| 2005/0149190 A1 | 7/2005 | Reiley |
| 2005/0159746 A1 | 7/2005 | Grob et al. |
| 2005/0165484 A1 | 7/2005 | Ferree et al. |
| 2005/0177240 A1 | 8/2005 | Blain |
| 2005/0187560 A1 | 8/2005 | Dietzel et al. |
| 2005/0192589 A1 | 9/2005 | Raymond et al. |
| 2005/0203532 A1 | 9/2005 | Ferguson et al. |
| 2005/0203533 A1 | 9/2005 | Ferguson et al. |
| 2005/0222683 A1 | 10/2005 | Berry |
| 2005/0228500 A1 | 10/2005 | Kim et al. |
| 2005/0234552 A1 | 10/2005 | Reiley |
| 2005/0235508 A1 | 10/2005 | Augostino et al. |
| 2005/0240264 A1 | 10/2005 | Tokish, Jr. et al. |
| 2005/0240265 A1 | 10/2005 | Kuiper et al. |
| 2005/0240266 A1 | 10/2005 | Kuiper et al. |
| 2005/0251256 A1 | 11/2005 | Reiley |
| 2005/0261770 A1 | 11/2005 | Kuiper et al. |
| 2005/0267579 A1 | 12/2005 | Reiley et al. |
| 2005/0273167 A1 | 12/2005 | Triplett et al. |
| 2005/0277922 A1 | 12/2005 | Trieu et al. |
| 2005/0283238 A1 | 12/2005 | Reiley |
| 2006/0009847 A1 | 1/2006 | Reiley |
| 2006/0009848 A1 | 1/2006 | Reiley |
| 2006/0009849 A1 | 1/2006 | Reiley |
| 2006/0025769 A1 | 2/2006 | Dick et al. |
| 2006/0029186 A1 | 2/2006 | De Villiers et al. |
| 2006/0036246 A1 | 2/2006 | Carl et al. |
| 2006/0041311 A1 | 2/2006 | McLeer |
| 2006/0041314 A1 | 2/2006 | Millard |
| 2006/0052785 A1 | 3/2006 | Augostino et al. |
| 2006/0058790 A1 | 3/2006 | Carl et al. |
| 2006/0058791 A1 | 3/2006 | Broman et al. |
| 2006/0079895 A1 | 4/2006 | McLeer |
| 2006/0079896 A1 | 4/2006 | Kwak et al. |
| 2006/0084991 A1 | 4/2006 | Borgstrom et al. |
| 2006/0085010 A1 | 4/2006 | Lieberman |
| 2006/0085072 A1 | 4/2006 | Funk et al. |
| 2006/0085075 A1 | 4/2006 | McLeer |
| 2006/0100707 A1 | 5/2006 | Stinson et al. |
| 2006/0100709 A1 | 5/2006 | Reiley |
| 2006/0106398 A1 | 5/2006 | Lauryssen et al. |
| 2006/0122703 A1 | 6/2006 | Aebi et al. |
| 2006/0149375 A1 | 7/2006 | Yuan et al. |
| 2006/0184180 A1 | 8/2006 | Augostino et al. |
| 2006/0200130 A1 | 9/2006 | Hawkins et al. |
| 2006/0217718 A1 | 9/2006 | Chervitz et al. |
| 2006/0241532 A1 | 10/2006 | Murakami et al. |
| 2006/0265070 A1 | 11/2006 | Stinson et al. |
| 2006/0271046 A1 | 11/2006 | Kwak et al. |
| 2007/0079517 A1 | 4/2007 | Augostino et al. |
| 2007/0088358 A1 | 4/2007 | Yuan et al. |
| 2007/0239159 A1 | 10/2007 | Altarac et al. |
| 2007/0276370 A1 | 11/2007 | Altarac et al. |
| 2007/0282344 A1 | 12/2007 | Yedlicka et al. |
| 2008/0039866 A1 | 2/2008 | Stetz et al. |
| 2009/0036925 A1 | 2/2009 | Sala et al. |

FOREIGN PATENT DOCUMENTS

| | | |
|---|---|---|
| DE | 10312755 A1 | 10/2003 |
| EP | 1103226 | 5/2001 |
| EP | 1205152 A1 | 5/2002 |
| EP | 1254639 A1 | 11/2002 |
| FR | 2726459 | 5/1996 |
| FR | 2749155 | 12/1997 |
| FR | 2844180 | 3/2004 |
| IE | S970323 | 6/1998 |
| JP | 59010807 A | 1/1984 |
| JP | 08252264 | 10/1996 |
| JP | 10082605 A | 3/1998 |
| JP | 10179622 A | 7/1998 |
| JP | 2004500953 | 1/2004 |
| WO | WO 95/05783 A1 | 3/1995 |
| WO | WO 96/00049 A1 | 1/1996 |
| WO | WO 98/48717 A1 | 11/1998 |
| WO | WO 98/56301 A1 | 12/1998 |
| WO | WO 99/05995 A1 | 2/1999 |
| WO | WO 99/23963 A1 | 5/1999 |
| WO | WO 99/60957 A1 | 12/1999 |
| WO | WO 99/65412 A1 | 12/1999 |
| WO | WO 00/38582 A1 | 7/2000 |
| WO | WO 00/62684 A1 | 10/2000 |
| WO | WO 01/06939 A1 | 2/2001 |
| WO | WO 01/15638 A1 | 3/2001 |
| WO | WO 01/28442 A1 | 4/2001 |
| WO | WO 01/30248 A1 | 5/2001 |
| WO | WO 01/39678 A1 | 6/2001 |
| WO | WO 01/67972 A2 | 9/2001 |
| WO | WO 01/97721 A2 | 12/2001 |
| WO | WO 02/00270 A1 | 1/2002 |
| WO | WO 02/00275 A1 | 1/2002 |
| WO | WO 02/02024 A1 | 1/2002 |
| WO | WO 02/02158 A1 | 1/2002 |
| WO | WO 02/34150 A2 | 5/2002 |
| WO | WO 02/43603 A1 | 6/2002 |
| WO | WO 02/071960 A1 | 9/2002 |
| WO | WO 02/089712 A1 | 11/2002 |
| WO | WO 03/020143 A1 | 3/2003 |
| WO | WO 03/041618 A2 | 5/2003 |
| WO | WO 03/075805 A1 | 9/2003 |
| WO | WO 03/101350 A1 | 12/2003 |
| WO | WO 2004/071358 A1 | 8/2004 |
| WO | WO 2004/103227 A1 | 12/2004 |
| WO | WO 2004/103228 A1 | 12/2004 |
| WO | WO 2005/009301 A1 | 2/2005 |
| WO | WO 2005/079711 A1 | 9/2005 |

OTHER PUBLICATIONS

Hewko, Brian; U.S. Appl. No. 12/377,552 entitled "Spinal implant," filed Feb. 13, 2009.

Reiley et al; U.S. Appl. No. 11/577,923 entitled "Crossbar spinal prosthesis having a modular design and systems for treating spinal pathologies" filed Apr. 25, 2007.

McLeer, Thomas, U.S. Appl. No. 11/934,724 entitled "Polymeric Joint Complex and Methods of Use" filed Nov. 2, 2007.

McLeer, Thomas, U.S. Appl. No. 11/934,720 entitled "Polymeric Joint Complex and Methods of Use" filed Nov. 2, 2007.

McLeer, Thomas, U.S. Appl. No. 11/934,719 entitled "Polymeric Joint Complex and Methods of Use" filed Nov. 2, 2007.

Reiley, Mark, U.S. Appl. No. 11/934,713 entitled "Facet arthroplasty devices and methods" filed Nov. 2, 2007.

Reiley, Mark, U.S. Appl. No. 11/939,540 entitled "Facet arthroplasty devices and methods" filed Nov. 13, 2007.

Reiley, Mark, U.S. Appl. No. 11/943,458 entitled "Facet arthroplasty devices and methods" filed Nov. 20, 2007.

Reiley, Mark, U.S. Appl. No. 11/949,007 entitled "Facet arthroplasty devices and methods" filed Nov. 30, 2007.

Reiley, Mark, U.S. Appl. No. 11/949,000 entitled "Facet arthroplasty devices and methods" filed Nov. 30, 2007.

Reiley et al.; U.S. Appl. No. 11/948,963 entitled "Prostheses, systems and methods for replacement of natural facet joints with artificial facet joint surfaces" filed Nov. 30, 2007.

Reiley, Mark, U.S. Appl. No. 11/957,208 entitled "Facet arthroplasty devices and methods" filed Dec. 14, 2007.
Reiley et al.; U.S. Appl. No. 11/957,315 entitled "Prostheses, systems and methods for replacement of natural facet joints with artificial facet joint surfaces" filed Dec. 14, 2007.
Reiley, Mark; U.S. Appl. No. 11/957,175 entitled "Facet arthroplasty devices and methods" filed Dec. 14, 2007.
Reiley et al.; U.S. Appl. No. 11/957,290 entitled "Prostheses, systems and methods for replacement of natural facet joints with artificial facet joint surfaces" filed Dec. 14, 2007.
Reiley, Mark; U.S. Appl. No. 11/956,961 entitled "Facet arthroplasty devices and methods" filed Dec. 14, 2007.
Reiley, Mark; U.S. Appl. No. 11/957,149 entitled "Facet arthroplasty devices and methods" filed Dec. 14, 2007.
Reiley, Mark; U.S. Appl. No. 11/957,061 entitled "Facet arthroplasty devices and methods" filed Dec. 14, 2007.
Reiley et al.; U.S. Appl. No. 11/957,259 entitled "Prostheses, systems and methods for replacement of natural facet joints with artificial facet joint surfaces" filed Dec. 14, 2007.
Reiley, Mark; U.S. Appl. No. 12/016,177 entitled "Facet arthroplasty devices and methods" filed Jan. 17, 2008.
Kuiper et al.; U.S. Appl. No. 11/948,994 entitled "Crossbar spinal prosthesis having a modular design and related implantation methods" filed Nov. 30, 2007.
Kuiper et al.; U.S. Appl. No. 11/948,973 entitled "Crossbar spinal prosthesis having a modular design and related implantation methods" filed Nov. 30, 2007.
Kuiper et al.; U.S. Appl. No. 11/957,303 entitled "Crossbar spinal prosthesis having a modular design and related implantation methods" filed Nov. 30, 2007.
McLeer, Thomas; U.S. Appl. No. 11/952,988 entitled "Polymeric joint complex and methods of use" filed Dec. 7, 2007.
Yuan et al.; U.S. Appl. No. 12/027,899 entitled "Prostheses, tools and methods for replacement of natural facet joints with artificial facet joint surfaces," filed Feb. 7, 2008.
Reiley et al; U.S. Appl. No. 12/058,403 entitled "Polyaxial adjustment of facet joint prostheses," filed Mar. 28, 2008.
Yuan et al; U.S. Appl. No.11/636,252 entitled "Prostheses, Tools, and Methods for Replacement of Natural Facet Joints with Artificial Facet Joint Surfaces" filed Dec. 8, 2006.
Ohrt et al; U.S. Appl. No. 11/724,927 entitled "Facet and disc arthroplasty system and method" filed Mar. 15, 2007.
Kuiper et al; U.S. Appl. No. 11/635,853, entitled "Crossbar Spinal Prosthesis Having a Modular Design and Related Implantation Methods", filed Dec. 8, 2008.
Reiley et al; U.S. Appl. No. 11/746,027 entitled "Facet Arthroplasty Devices and Methods," filed May 8, 2007.
Reiley et al; U.S. Appl. No. 11/577,872 entitled "Facet Joint Prosthesis" which entered the U.S. from the National Phase Apr. 24, 2007.
Reiley et al; U.S. Appl. No. 11/577,923 entitled "Facet Joint Prostheses" filed Apr. 25, 2007.
Kuiper et al; U.S. Appl. No. 11/577,964 entitled "Crossbar Spinal Prosthesis Having a Modular Design and Systems for Treating Spinal Pathologies," filed Apr. 25, 2007.
Kuiper et al; U.S. Appl. No. 11/577,967 entitled "Crossbar Spinal Prosthesis having a Modular Design and Systems for Treating Spinal Pathologies," filed Apr. 25, 2007.
Reiley, Mark; U.S. Appl. No. 11/750,981 entitled "Facet Arthroplasty Device and Methods," filed May 18, 2007.
Berg, et al; U.S. Appl. No. 11/800,895 entitled "Minimally Invasive Spine Restoration Systems, Devices, Methods, and Kits," filed May 7, 2007.
Abraham, D.J. et al. "Indications and Trends in Use in Cervical Spinal Fusions." Orthop Clin North Am. Oct. 1998; 29(4):731-44.
Eichholz, K.M. et al. "Complications of Revision Spinal Surgery", Neurosurg Focus; (Sep. 15, 2003), 15(3): pp. 1-4.
Farfan, H.F. Effects of Torsion on the Intervertebral Joints. The Canadian Journal of Surgery, Jul. 1969; 12(3);338-41.
Farfan, H.F. et al. "The Relation of Facet Orientation to Intervertebral Disc Failure." The Canadian Journal of Surgery, Apr. 1967; 10(2):179-85.
Farfan, H.F. The Pathological Anatomy of Degenerative Spondylolisthesis. A Cadaver Study. Spine. Sep.-Oct. 1980; 5(5):412-8.
Fosbinder, R.A. et al. Essentials of Radiologic Science. The McGraw-Hill Companies; 2002.
Goh, J.C. et al. "Influence of PLIF cage size on lumbar spine stability." Spine. Jan. 2000, 25(1) Medline abstract (one page).
Guyer R. et al. "Impliant: Motion Preservation through Total Posterior-Element Replacement." May 7, 2004 Presentation held at Hofburg Center, Vienna, Austria, (2 pages).
Head, W.C. "Wagner surface replacement arthroplasty of the hip." Analysis of fourteen failures in forty-one hips. J Bone Joint Surg. Am; Mar. 1981, 63(3), Medline abstract (one page).
Khoo, L.T. et al. "A biomechanical analysis of the effects of lumbar fusion on the adjacent vetebral motion segment." Proceedings of the 2000 Annual Meeting of the North American Spine Society, New Orleans, pp. 127-128.
Kirkaldy-Willis, W.H. et al. "Pathology and Pathogenesis of Lumbar Spondylosis and Stenosis." Spine. Dec. 1978; 3(4):319-28.
Kotani, Y. et al. The effects of spinal fixation and destabilization on the biomechanical and histologic properties of spinal ligaments. An in vivo study. Spine, Mar. 15, 1998, 23(6), Medline abstract (2 pages).
Kulkarni, et al. "Accelerated Spondylotic Changes Adjacent to the Fused Segment Following Central Cervical Corpectomy: Magnetic Resonance Imaging Study Evidence." J. Neurosurg (Spine 1). 2004; 100: 2-6.
Lam, K. N., et al. X-ray "Diagnosis: A Physician's Approach." Springer-Verlag; 1998.
Lemaire, J.P. et al. "Intervertebral disc prosthesis: results and prospects for the year 2000." Clinical Orthopaedics and Related Research. 1997; No. 337, pp. 64-76.
Lombardi, J.S. et al. "Treatment of Degenerative Spondylolisthesis." Spine. 1985; 10(9): 821-7.
McMillin, C. R. et al. Artificial Spinal Discs with up to Five Years Follow-up. 20th Annual Meeting of the Society for Biomaterials (Abstract) 1994; p. 89.
Nagata, H. et al. "The effects of immobilization of long segments of the spine on the adjacent and distal facet force and lumbrosacral motion". Spine, Dec. 1993; 18(16):2471-2479, (9 pages).
Nibu, K. et al. "Multidirectional stabilizing potential of BAK interbody spinal fusion system for anterior surgery." J Spinal Discord, Aug. 1997; 10(4), Medline abstract (one page).
Posner, I. et al. A "Biomechanical Analysis of the Clinical Stability of the Lumbar and Lumbosacral Spine." Spine. 1982: 7(4): 374-389.
Rosenberg, N.J. "Degenerative Spondylolisthesis. Predisposing Factors." The Journal of Bone and Joint Surgery. 1975; 57-A(4): 467-74.
Sacher, R., Impllant Brochure for presentation at MedTech Insight Conference (Oct. 31, 2003) Boston, MA. pp. 93-94.
Slone, R. M. et al. Body CT: A Practical Approach. The McGraw-Hill Companies; 1999.
Stout, G. H. et al. X-Ray Structure Determination: A Practical Guide. 2nd Edition. John Wiley & Sons; 1989.
Szpalski, M., et al. Spine Arthroplasty: A Historical Review. Eur Spine J. 2002; 11(Suppl. 2): S65-S84.
Tsantrizos, A. et al. "Segmental stability and compressive strength of posterior lumbar interbody fusion Implants." Spine, Aug. 1, 2000; 25(15), Medline abstract (one page).
UCR Pedicle Screw System from SeaSpine (Information available at http://www.seaspine.com/UCR_Pedicle_Screw_System.html). Accessed Dec. 5, 2005.
Victrex of Lancashire, Great Britain. (Information on Vlctrex available at http://www.matweb.com). Accessed Dec. 5, 2005.
Quest et al.; U.S. Appl. No. 12/099,068 entitled "Measurement and trialing system and methods for orthopedic device component selection," filed Apr. 7, 2008.
Reiley, Mark; U.S. Appl. No. 12/176,280 entitled "Facet arthroplasty devices and methods," filed Jul. 18, 2008.
Yuan et al; U.S. Appl. No. 12/163,738 entitled "Prostheses, tools and methods for replacement of natural joints with artificial facet joint surfaces," filed Jun. 27, 2008.

Funk et al; U.S. Appl. No. 12/186,461 entitled "Implantable orthopedic device component selection instrument and methods," filed Aug. 5, 2008.

Reiley, Mark; U.S. Appl. No. 11/839,434 entitled "Facet arthroplasty devices and methods", filed Aug. 15, 2007.

Reiley, Mark; U.S. Appl. No. 11/824,012 entitled "Facet arthroplasty device and methods," filed Jun. 29, 2007.

Reiley, Mark; U.S. Appl. No. 11/831,870 entitled "Prostheses systems and methods for replacement of natural facet joints with artificial facet joint surfaces," filed Jul. 31, 2007.

Ralph et al; U.S. Appl. No. 11/837,335 entitled "Angled Washer Polyaxial Connection for Dynamic Spine Prosthesis," filed Aug. 10, 2007.

Reiley, Mark; U.S. Appl. No. 11/775,174 entitled "Facet arthroplasty devices and methods," filed Jul. 9, 2007.

Stone et al; U.S. Appl. No. 11/861,239 entitled "Facet Replacement Device Removal and Revision Systems and Methods" filed Sep. 25, 2007.

* cited by examiner

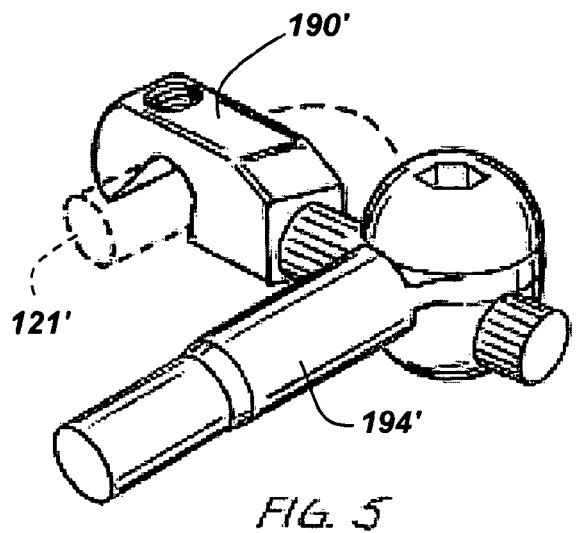
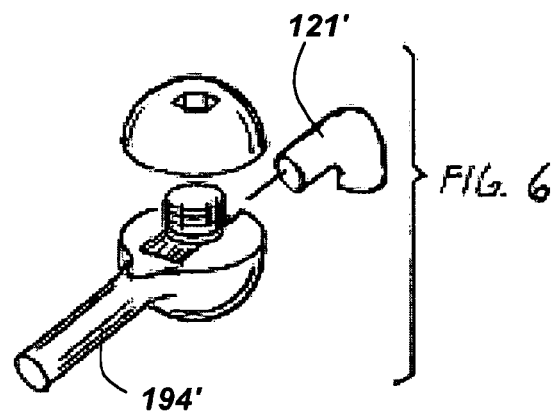
FIG. 5
FIG. 6
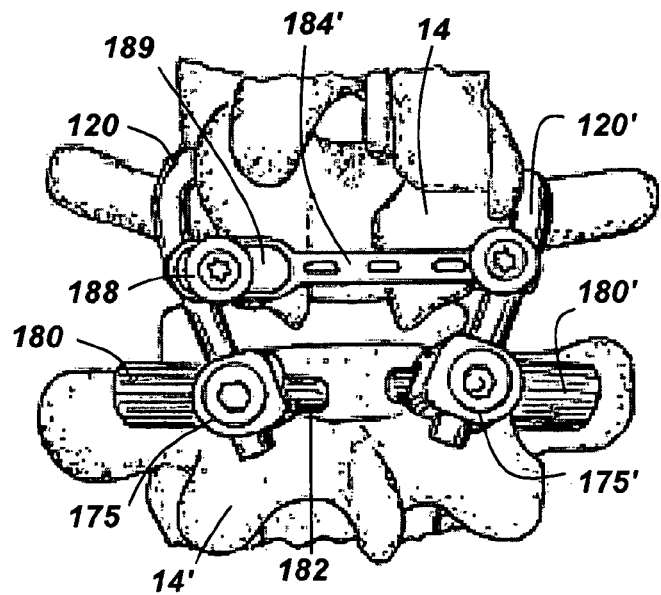
FIG. 7

ARTHROPLASTY REVISION SYSTEM AND METHOD

CROSS-REFERENCE TO RELATED APPLICATIONS

This application is a continuation-in-part of commonly assigned U.S. patent application Ser. No. 11/206,676, filed Aug. 17, 2005, which is a continuation-in-part of commonly assigned U.S. patent application Ser. No. 11/071,541, filed Mar. 2, 2005, the disclosures of which are incorporated herein. This application also claims the benefit of U.S. Provisional Patent Application Ser. Nos. 60/752,277, filed Dec. 20, 2005, and 60/847,013, filed Sep. 25, 2006, the disclosures of which are incorporated herein.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention generally relates to devices and surgical methods for treatment of various spinal pathologies. More specifically, the present invention is directed to configurable and anatomically adaptable implantable devices for use in a spine and surgical procedures for altering the biomechanics of a spine, either temporarily or permanently. The devices alter, replace and/or revise existing anatomy and/or previously implanted devices.

BACKGROUND OF THE INVENTION

Back pain, particularly in the small of the back, or lumbosacral region (L4-S1) of the spine, is a common ailment. In many cases, the pain severely limits a person's functional ability and quality of life. Back pain interferes with work, routine daily activities, and recreation. It is estimated that Americans spend $50 billion each year on low back pain alone. It is the most common cause of job-related disability and a leading contributor to missed work.

Through disease or injury, the laminae, spinous process, articular processes, facets and/or facet capsules of one or more vertebral bodies along with one or more intervertebral discs can become damaged, which can result in a loss of proper alignment or loss of proper articulation of the vertebra. This damage can also result in an anatomical change, loss of mobility, and pain or discomfort. For example, the vertebral facet joints can be damaged by traumatic injury or as a result of disease. Diseases damaging the spine and/or facets include osteoarthritis where the cartilage of joints is gradually worn away and the adjacent bone is remodeled, ankylosing spondylolysis (or rheumatoid arthritis) of the spine which can lead to spinal rigidity, and degenerative spondylolisthesis which results in a forward displacement of the lumbar vertebra on the sacrum. Damage to facet joints of the vertebral body often results in pressure on nerves, commonly referred to as "pinched" nerves, or nerve compression or impingement. The result is pain, misaligned anatomy, a change in biomechanics and a corresponding loss of mobility. Pressure on nerves can also occur without facet joint pathology, e.g., as a result of a herniated disc.

One conventional treatment of facet joint pathology is spine stabilization, also known as intervertebral stabilization. Intervertebral stabilization desirably controls, prevents or limits relative motion between the vertebrae through the use of spinal hardware, removal of some or all of the intervertebral disc, fixation of the facet joints, bone graft/osteo-inductive/osteo-conductive material positioned between the vertebral bodies (with or without concurrent insertion of fusion cages), and/or some combination thereof, resulting in the fixation of (or limiting the motion of) any number of adjacent vertebrae to stabilize and prevent/limit/control relative movement between those treated vertebrae.

Although spine fusion surgery is an efficacious treatment, complications can nonetheless result. Patients undergoing spine surgery frequently continue to experience symptoms. For surgical procedures in the lumbar spine, failure rates as high as 37% have been reported after lumbar fusion and 30% for surgery without fusion. See Eichholz, et al., "Complications of Revision Spinal Surgery," *Neurosurg Focus* 15(3):1-4 (2003). Post-operative problems can include decompression related problems, and fusion related problems. Decompression related problems (i.e., loss of normal spine balance resulting in the head and trunk no longer being centered over the pelvis) include, for example, recurrent disc herniation, spinal stenosis, chronic nerve injury, infection, and decompression. Fusion related problems can include, pain from the bone harvest site, failure of a fusion to develop, loosening of the implanted devices, nerve irritation caused by the devices, infection, and poor alignment of the spine.

Stabilization of vertebral bodies can also be achieved (to varying degrees) from a wide variety of procedures, including the insertion of motion limiting devices (such as intervertebral spacers, artificial ligaments and/or dynamic stabilization devices), devices promoting arthrodesis (rod and screw systems, cables, fusion cages, etc.), and complete removal of some or all of a vertebral body from the spinal column (which may be due to extensive bone damage and/or tumorous growth inside the bone) and insertion of a vertebral body replacement (generally anchored into the adjacent upper and lower vertebral bodies). Various devices are known for fixing the spine and/or sacral bone adjacent the vertebra, as well as attaching devices used for fixation, including devices disclosed in: U.S. Pat. Nos. 6,585,769; 6,290,703; 5,782,833; 5,738,585; 6,547,790; 6,638,321; 6,520,963; 6,074,391; 5,569,247; 5,891,145; 6,090,111; 6,451,021; 5,683,392; 5,863,293; 5,964,760; 6,010,503; 6,019,759; 6,540,749; 6,077,262; 6,248,105; 6,524,315; 5,797,911; 5,879,350; 5,885,285; 5,643,263; 6,565,565; 5,725,527; 6,471,705; 6,554,843; 5,575,792; 5,688,274; 5,690,630; 6,022,350; 4,805,602; 5,474,555; 4,611,581; 5,129,900; 5,741,255; 6,132,430; and U.S. Patent Publication No. 2002/0120272.

More recently, various treatments have been proposed and developed as alternatives to spinal fusion. Many of these treatments seek to restore (and/or maintain) some, or all, of the natural motion of the treated spinal unit, and can include intervertebral disc replacement, nucleus replacement, facet joint resurfacing, and facet joint replacement. Such solutions typically include devices that do not substantially impair spinal movement. See, U.S. Pat. Nos. 6,610,091; 6,811,567; 6,902,580; 5,571,171; and Re 36,758; and PCT Publication Nos. WO 01/158563, WO 2004/103228, WO 2005/009301, and WO 2004/103227. Thus, spinal arthroplasty has become an acceptable alternative to fusion, particularly in cases of degenerative disc disease. Arthroplasty devices can be particularly useful because the devices are designed to create an artificial joint or restore the functional integrity and power of a joint.

SUMMARY OF THE INVENTION

It may be necessary to alter or revise an implanted spinal prosthesis or fusion device. For example, due to the continued progress of spine disease, a spine surgeon may need to remove part or all of a previously implanted arthroplasty device in order to provide access to the patient's vertebra(e) and/or disc. After performing a surgical procedure on the patient (e.g., implantation of an artificial disc, resection of the lamina, etc.), the surgeon may want to provide the patient with a prosthesis to replace the function of the original device or to perform an entirely new function. It would be desirable to use a remaining portion of the implanted arthroplasty device as part of the new prosthesis.

In another example, even if no portion of an implanted device is removed, it may be desirable to revise the biomechanical function of the implanted device. For example, an implanted arthroplasty device may permit movement between the adjacent vertebrae to which it is attached. It may be desirable to change, limit or completely eliminate the motion between the cephalad and caudal portions of the prosthesis, thereby changing, limiting or eliminating movement between the vertebrae, without removal, or with only partial removal, of the existing implant. It would therefore be desirable to add a revision device to the arthroplasty implant to change the implant's biomechanics.

One aspect of the invention provides a method of revising an implanted arthroplasty device, such as an implanted arthroplasty device having a cephalad component fixed to a first vertebra and a caudal component fixed to a second vertebra inferior to the first vertebra. The method includes the following steps: removing a portion of a previously implanted spinal arthroplasty device; and attaching a revision component to a remaining portion of the previously implanted spinal arthroplasty device to alter a biomechanical characteristic of the implanted arthroplasty device. In some embodiments, wherein the caudal component includes a caudal cup, the removing step includes the step of removing the caudal cup from a fixation element. The attaching step may also include the step of attaching an attachment device to the caudal cup fixation element.

In some embodiments, wherein the cephalad component includes a cephalad arm and a cephalad bearing element, the removing step includes the step of removing the cephalad bearing element from the cephalad arm. The attaching step may also include the step of attaching a connector housing to the cephalad arm and attaching the connector housing to an other arthroplasty element (such as the caudal component) or revision component. The removing step may also include the step of removing a caudal cup from a caudal fixation element, with the attaching step including the step of attaching a caudal attachment device to the caudal fixation element and attaching the housing to the caudal attachment device. In situations in which the cephalad component has two cephalad arms, the attaching step may include the step of attaching a crossbar to the two cephalad arms.

In embodiments in which the cephalad component has an implanted cephalad arm, the removing step may include the step of removing a portion of the implanted cephalad arm. The attaching step may also include the step of attaching a new cephalad arm to a remaining portion of the implanted cephalad arm, such as by attaching a connector housing to the new cephalad arm and attaching the connector housing to an other arthroplasty device element (such as the caudal component) or a revision component. The new cephalad arm may be located medial to or lateral to the implanted cephalad arm. The removing step further may also include the step of removing a caudal cup from a caudal fixation element, with the attaching step including the step of attaching a caudal attachment device to the caudal fixation element and attaching the housing to the caudal attachment device. In situations in which the cephalad component has two implanted cephalad arms, the removing step may include the step of removing a portion of each implanted cephalad arm and the attaching step may includes the steps of attaching a new cephalad arm to a remaining portion of each implanted cephalad arm and attaching a crossbar to the two new cephalad arms.

Another aspect of the invention provides a method of altering the biomechanics between first and second vertebrae including the steps of accessing an implanted spinal device (such as, e.g., a spinal arthroplasty device, a facet joint replacement device, a dynamic stabilization device, in interspinous space, and/or an artificial disc) comprising a cephalad component fixed to the first vertebra and a caudal component fixed to the second vertebra inferior to the first vertebra, the cephalad and caudal components having a biomechanical relationship (such as, e.g., a range of motion) between them, and attaching a revision component to the cephalad and caudal components to alter the biomechanical relationship (e.g., by reducing the range of motion). In some embodiments, the attaching step substantially eliminates motion between the cephalad and caudal components. In embodiments in which the cephalad component has a cephalad bearing element and the caudal component has a caudal bearing element, the attaching step may include the step of attaching a revision component extending from one side of the cephalad bearing element to an opposing side of the caudal bearing element. In embodiments in which the cephalad component further includes a cephalad arm, the attaching step may also include the step of attaching the revision component to the cephalad arm.

Yet another aspect of the invention provides a revision device for an implanted spinal arthroplasty device, where the implanted spinal arthroplasty device has a cephalad component fixed to a first vertebra and a caudal component fixed to a second vertebra inferior to the first vertebra. The revision device according to this aspect of the invention has an attachment component adapted to attach to a remaining portion of an arthroplasty device component after a portion of the arthroplasty device has been removed to alter a biomechanical characteristic of the arthroplasty device. In some embodiments in which the caudal component of the implanted arthroplasty device has a caudal cup, the revision device has a caudal attachment device adapted to be attached to a caudal cup fixation element after the caudal cup has been removed.

In embodiments in which the cephalad component of the implanted arthroplasty device has a cephalad arm, the revision device may have a connector housing adapted to be attached to the cephalad arm and to an other arthroplasty device element (such as the caudal component) or a revision component. In some embodiments, the revision device also includes a caudal attachment device adapted to be attached to a caudal cup fixation element after the caudal cup has been removed, the connector housing being adapted to be attached to the caudal attachment device. In some embodiments, the revision device has a cross-bar adapted to attach to two cephalad arms of the implanted spinal arthroplasty device.

In embodiments in which the implanted spinal arthroplasty device has a cephalad arm, the revision device may also include a new cephalad arm and an attachment mechanism adapted to attach the new cephalad arm to a remaining portion of the implanted cephalad arm (medially or laterally of the implanted cephalad arm) after a portion of the implanted cephalad arm has been removed. In such embodiments, the revision device may also have a connector housing attached to the new cephalad arm and being adapted to attach to an other arthroplasty device element (such as the caudal component) or revision device element. The revision device may also have a caudal attachment device adapted to be attached to a caudal cup fixation element after the caudal cup has been removed, the connector housing being adapted to be attached to the caudal attachment device. In embodiments in which the implanted spinal arthroplasty device has two cephalad arms, the revision device may have two new cephalad arms, each having an attachment mechanism adapted to attach one of the new cephalad arms to a remaining portion of a respective implanted cephalad arm after a portion of such implanted cephalad arm has been removed.

Still another aspect of the invention provides a revision device for an implanted spinal device (such as, e.g., a spinal arthroplasty device, a facet joint replacement device, a dynamic stabilization device, in interspinous space, and/or an artificial disc), where the implanted spinal arthroplasty device has a cephalad component fixed to a first vertebra and a caudal component fixed to a second vertebra inferior to the first vertebra, the cephalad and caudal components having a biomechanical relationship (such as, e.g., a range of motion) between them. The revision device according to this aspect of the invention includes a first surface adapted to interact with the cephalad component and a second surface adapted to interact with the caudal component to alter the biomechanical relationship (e.g., to limit motion) between the cephalad and caudal components. In some embodiments in which the cephalad component of the implanted spinal device has a cephalad bearing element and the caudal component has a caudal bearing element, the revision device is adapted to attach to the cephalad component on one side of the cephalad bearing element and to attach to the caudal component on a side of the caudal bearing element opposite to said one side to, e.g., limit or eliminate motion between the cephalad and caudal components. In embodiments in which the cephalad component also has a cephalad arm, the revision device may include an attachment mechanism adapted to attach to the cephalad arm.

Various other alternative aspects of the invention provide for the use of one or more revision devices for implanted spinal devices, such as spinal arthroplasty devices, motion limiting devices (such as intervertebral spacers, artificial ligaments and/or dynamic stabilization devices), devices promoting arthrodesis (rod and screw systems, cables, fusion cages, etc.), and/or vertebral replacement devices. The revision devices according to these aspects of the invention may include a linkage or linkages that serves to augment and/or replace a pre-existing connection between adjacent and/or non-adjacent vertebral bodies. Such devices can increase, decrease and/or alter the amount, range and/or quality of motion allowed or permitted between the targeted vertebral bodies, depending upon the desired surgical outcome, as well as the current condition and/or needs of the patient.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 5 shows details of an alternative connection mechanism to be used with the embodiment of FIG. 3.

FIG. 6 is an exploded view of yet another connection mechanism to be used with the embodiment of FIG. 3.

FIG. 7 shows an implanted spinal arthroplasty device that has been revised by a revision device according to yet another embodiment of the invention.

DETAILED DESCRIPTION OF THE INVENTION

Figure 1:
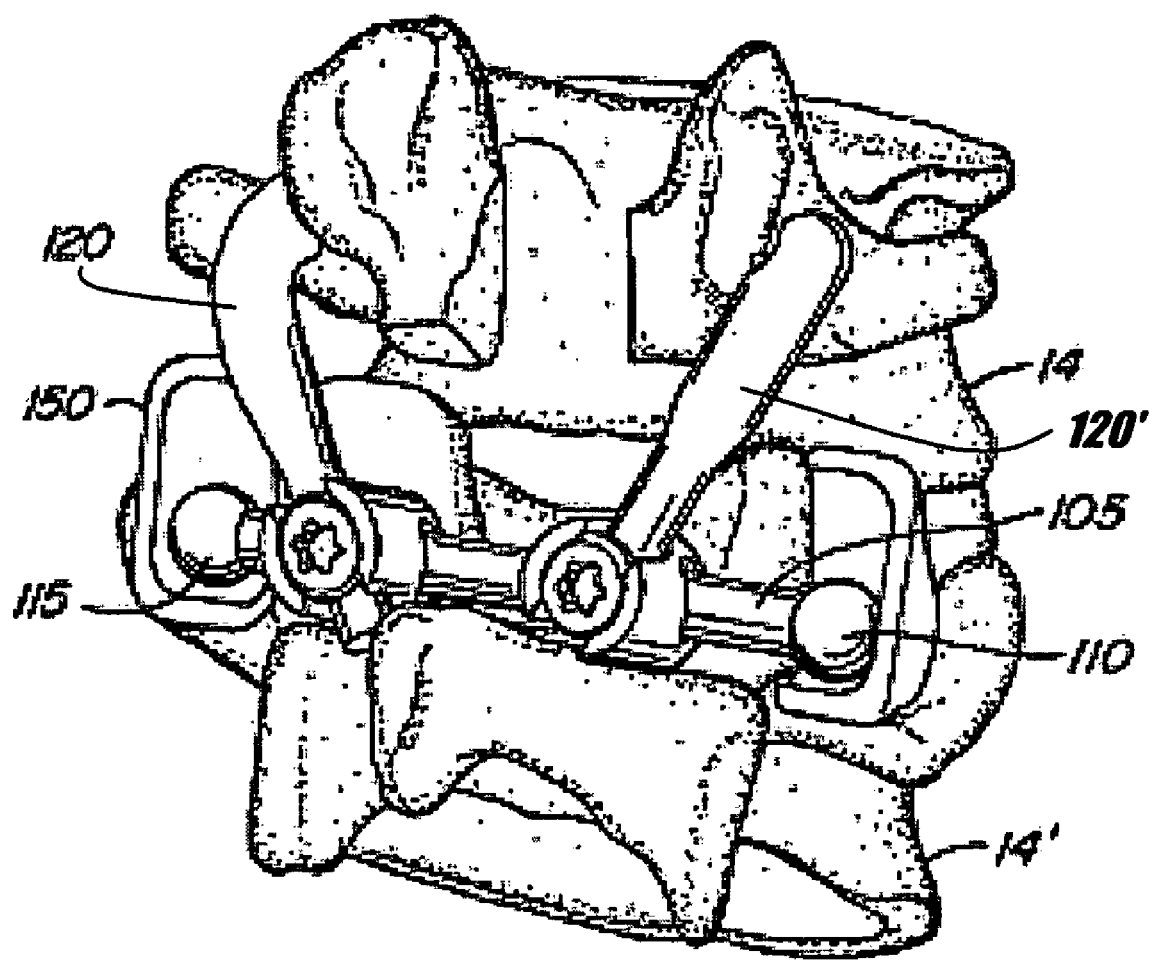
FIG. 1 is a perspective view of an implanted spinal arthroplasty device.

The revision devices and methods of this invention may be used with a variety of spinal implants, such as arthroplasty implants. FIG. 1 shows an exemplary spinal arthroplasty device attached to adjacent vertebrae 14 and 14'. The spinal arthroplasty device includes a crossbar 105, a pair of cephalad arms 120, 120' and a pair of caudal cups 150, 150'. Heads 110 and 115 at opposing ends of crossbar 105 interact with bearing surfaces inside caudal cups 150 and 150' to replace the articulating action of the patient's natural facet joints, which have been removed, when the patient flexes and extends his or her back. In this example, each cephalad arm 120, 120' attaches to the pedicle of the superior vertebra 14 as shown, via, e.g., a stem (not shown) inserted into the pedicle. The other ends of the cephalad arms attach to crossbar 105 via crossbar mounts 175 and 175'. The caudal cups 150 and 150' attach to the inferior vertebra 14' via, e.g., stems (not shown) inserted into the pedicles. Further details of this exemplary spinal arthroplasty device may be found in U.S. Ser. No. 11/206,676.

Figure 2:
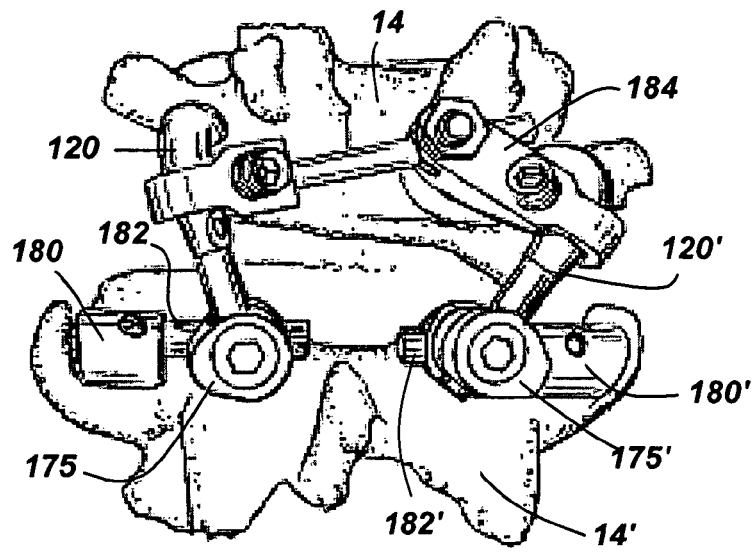
FIG. 2 shows an implanted spinal arthroplasty device that has been revised by a revision device according to on embodiment of the invention.

FIG. 2 shows an implanted spinal arthroplasty device that has been revised by a revision device. In this example, the revision device alters the biomechanics of the implanted device by substantially eliminating movement between the cephalad and caudal members and, thereby, between the adjacent vertebrae. The caudal cups that had been attached to inferior vertebra 14' have been removed from their stems, which remain implanted. The caudal cups may be removed, e.g., by grasping them with a grasping tool and/or through the application of energy (heat, vibration, ultrasound, etc.). In place of the caudal cups, attachment devices 180 and 180' are attached to the exposed portions of the caudal stems. Caudal attachment devices, such as rods 182 and 182', extend medially from attachment devices 180 and 180'. Alternatively, a single rod extending between attachment devices 180 and 180' may be used in place of shorter rods 182 and 182'.

As shown in FIG. 2, instead of attaching to a movable crossbar, cephalad arms 120 and 120' are now attached to the immovable caudal attachment devices via mounts 175 and 175' or other connectors or housings. Addition of the revision device therefore substantially eliminates movement between the remaining cephalad and caudal components of the implanted arthroplasty device and between vertebrae 14 and 14'. A crossbar 184 may be added between the cephalad arms for additional stability. The crossbar may have an adjustable length, as shown. Alternatively, the crossbar may have a fixed length and may possibly provide multiple cephalad arm attachment points selectable along its length, as shown, e.g., in FIG. 7 or FIG. 8.

Figure 3:
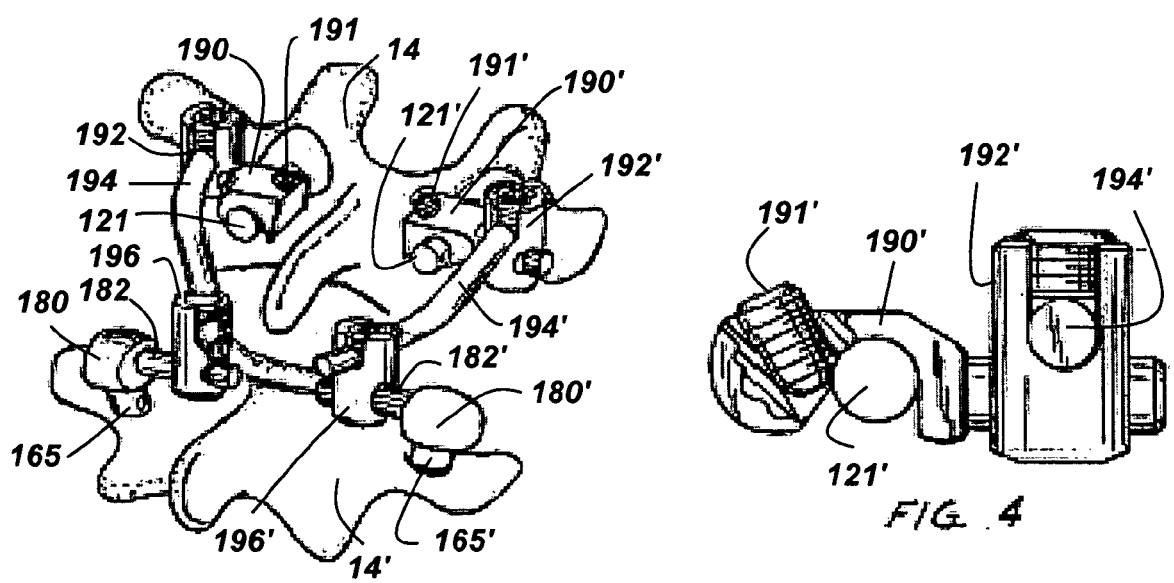
FIG. 3 shows an implanted spinal arthroplasty device that has been revised by a revision device according to another embodiment of the invention.
Figure 4:
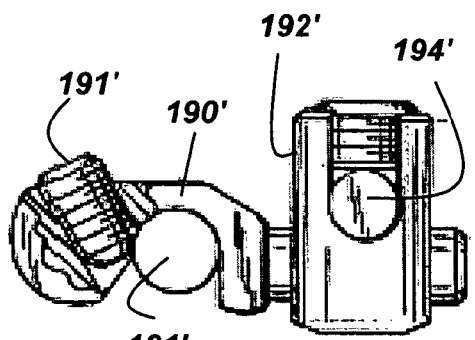
FIG. 4 shows details of one aspect of the embodiment of FIG. 3.

FIGS. 3 and 4 show a revision device according to another embodiment of the invention. As in the FIG. 2 embodiment, the caudal cups of the implanted arthroplasty device have been removed and replaced with attachment devices 180 and 180' attached to the implanted caudal stems 165 and 165'. Caudal attachment rods 182 and 182' extend from attachment devices 180 and 180'. In this embodiment, however, portions of the cephalad arms of the implanted arthroplasty device have been removed, e.g., to provide access to otherwise inaccessible portions of the spinal anatomy. Removal of such portions (or other components of the arthroplasty device) may be desirous to allow surgical access to selected anatomy (such as the intervertebral disk and/or other posterior anatomy for disc replacement and/or augmentation, and/or installation of fusion cages), removal of damaged, dislodged and/or loose portions or components, as well as those portions or components that may be causing undesirable anatomical effects (i.e., impinging upon nerves or other structures). The remaining portions 121 and 121' of the cephalad arms provide attachment points for the revision device. Specifically, cephalad attachment devices 190 and 190' attach to the cephalad arm portions by, e.g., set screws 191 and 191'. Two new cephalad arms 194 and 194' are attached to the cephalad attachment devices via attachment mounts or housings 192 and 192'. The new cephalad arms 194 and 194' attach to the caudal attachment rods 182 and 182' via mounts or connector housings 196 and 196'. As in the FIG. 2 embodiment, the revision device shown in FIGS. 3 and 4 alters the biomechanics of the implanted device by substantially eliminating movement between the cephalad and caudal members and, thereby, between the adjacent vertebrae. A crossbar (such as the crossbar shown in FIG. 2, 7 or 8) may be attached to the new cephalad arms to provide additional stability for the entire construct and/or for individual components relative to the construct (such as a loose cephalad arm).

FIGS. 5 and 6 show alternative connector housings for attaching the new cephalad arm to the remaining portion of the implanted cephalad arm. In FIG. 5, as in FIG. 3, the axis of the new cephalad arm is offset with respect to the axis of the remaining portion 121' of the implanted cephalad arm. In FIG. 6, the new cephalad arm 194' is substantially uniaxial with the remaining portion 121' of the implanted cephalad arm.

FIG. 7 is an embodiment similar to that of FIG. 2 and shows an implanted spinal arthroplasty device that has been revised by a revision device. As in the FIG. 2 embodiment, the revision device alters the biomechanics of the implanted device by substantially eliminating movement between the cephalad and caudal members and between the adjacent vertebrae. The caudal cups that had been attached to inferior vertebra 14' have been removed from their stems, which remain implanted. In place of the caudal cups, attachment devices 180 and 180' are attached to the exposed portions of the caudal stems. Caudal attachment devices, such as rods 182 and 182', extend medially from attachment devices 180 and 180'. Cephalad arms 120 and 120' are attached to the immovable caudal attachment rods via mounts 175 and 175' or other connectors or housings. Addition of the revision device therefore substantially eliminates movement between the remaining cephalad and caudal components of the implanted arthroplasty device and between vertebrae 14 and 14'. Crossbar 184 has been added between the cephalad arms for additional stability. In this embodiment, the point at which crossbar 184 attaches to cephalad arm 120 may be adjusted through the interaction of attachment screw 188 and crossbar slot 189.

Figure 8:
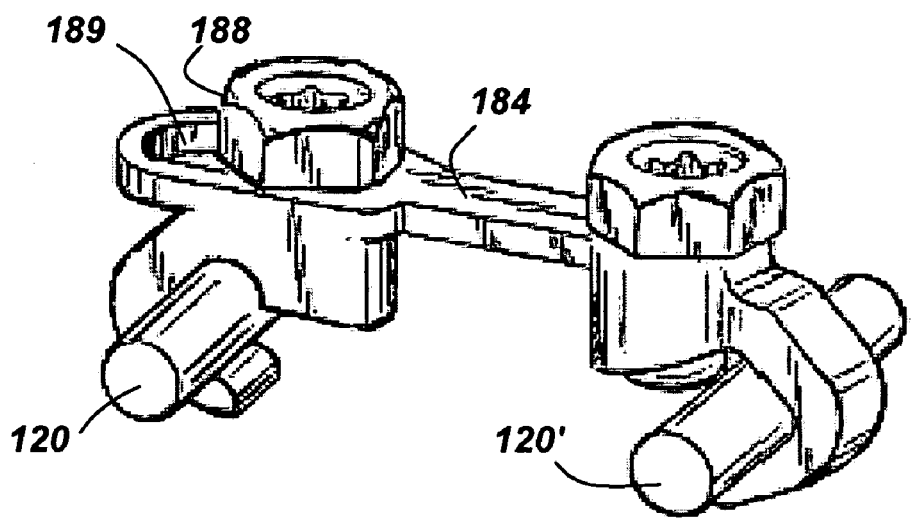
FIG. 8 shows details of a crossbar of a revision device attached to two cephalad arms.

FIG. 8 shows an alternative adjustable cephalad arm crossbar 184 for use in a spinal arthroplasty revision device. The effective length of crossbar 184 can be adjusted through the interaction of adjustment screw 188 and crossbar slot 189.

Figure 9:
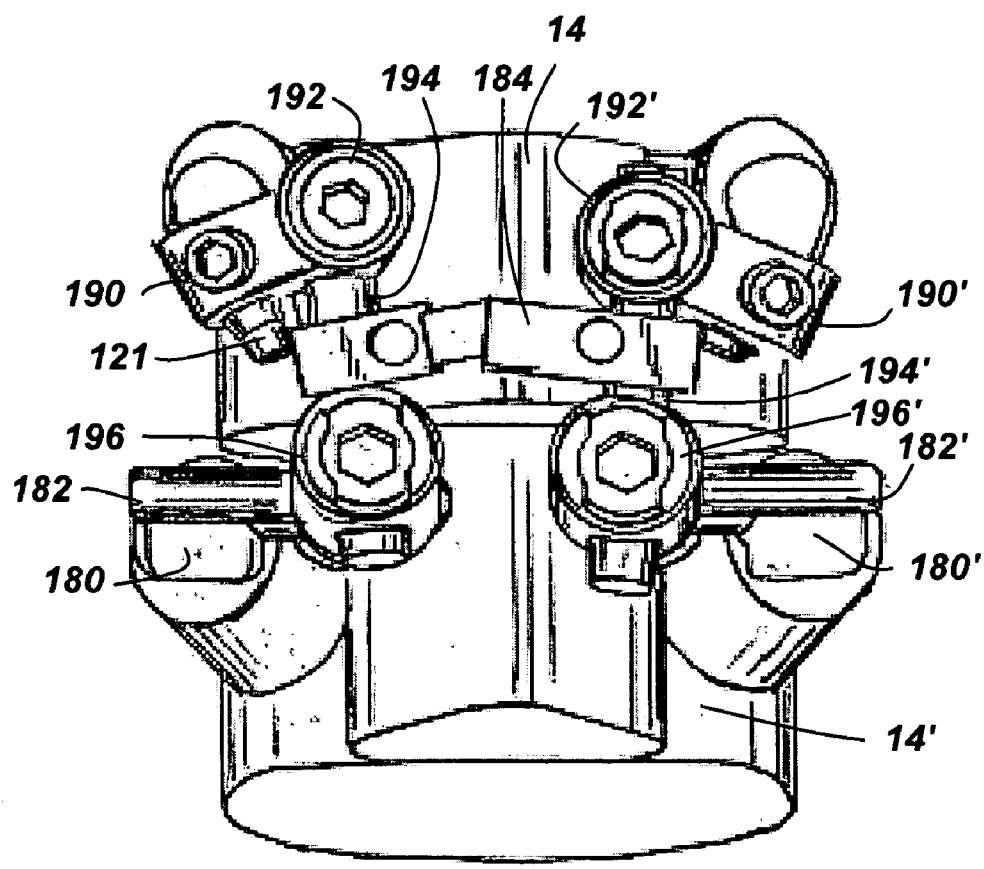
FIG. 9 shows an implanted spinal arthroplasty device that has been revised by a revision device according to yet another embodiment of the invention.

FIG. 9 shows yet another embodiment of a revision device attached to remaining portions 121 and 121' of removed cephalad arms of an implanted spinal arthroplasty device. As in other embodiments, the caudal cups of the implanted arthroplasty device have been removed and replaced with attachment devices 180 and 180' attached to the implanted caudal stems, and caudal attachment rods 182 and 182' extend from attachment devices 180 and 180'. As in the FIG. 3 embodiment, portions of the cephalad arms of the implanted arthroplasty device have been removed, e.g., to provide access to otherwise inaccessible portions of the spinal anatomy, and the remaining portions 121 and 121' of the cephalad arms provide attachment points for the revision device. Cephalad attachment devices 190 and 190' attach to the cephalad arm portions by, e.g., set screws 191 and 191'. Two new cephalad arms 194 and 194' are attached to the cephalad attachment devices via attachment mounts or housings 192 and 192'. Unlike the FIG. 3 embodiment in which the new cephalad arms are disposed lateral to the remaining portions of the implanted cephalad arms, in this embodiment the new cephalad arms 194 and 194' are medial to the remaining portions 121 and 121' of the implanted cephalad arms. Also, the new cephalad arms 194 and 194' attach to the caudal attachment rods 182 and 182' via mounts or connector housings 196 and 196' at locations medial to caudal attachment devices 180 and 180'. A crossbar 184 is attached to the new cephalad arms to provide additional stability. The revision device shown in FIG. 9 alters the biomechanics of the implanted device by substantially eliminating movement between the cephalad and caudal members and, thereby, between the adjacent vertebrae.

Figure 10:
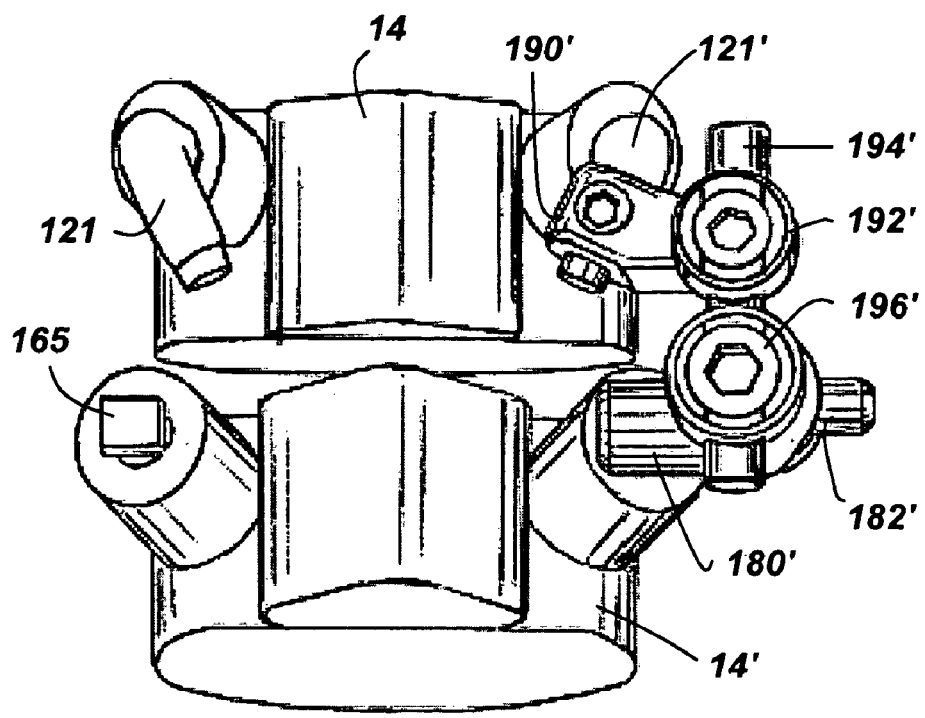
FIG. 10 shows an implanted spinal arthroplasty device that has been revised by a revision device according to still another embodiment of the invention.

FIG. 10 shows still another embodiment of a spinal arthroplasty revision device (including cephalad attachment device 190', new cephalad arm 194' and attachment housings 192' and 196') attached to only one side of the spine and lateral to both the implanted cephalad arm 121' and the caudal attachment device 180'. The remaining portion 121 of the other implanted cephalad arm and the other caudal stem 165 are not being used as part of the revision (although such portions could be utilized for the revision, if desired, or as anchoring points for other spinal hardware). Use of a lateral location for the revision device may be useful in cases where the patient's anatomy does not permit a medial position for the revision device due, e.g., to the size of the patient or to the limited amount of bone that had previously been removed and/or the location of the spinal cord/nerves and other anatomical structures.

Figure 11A:
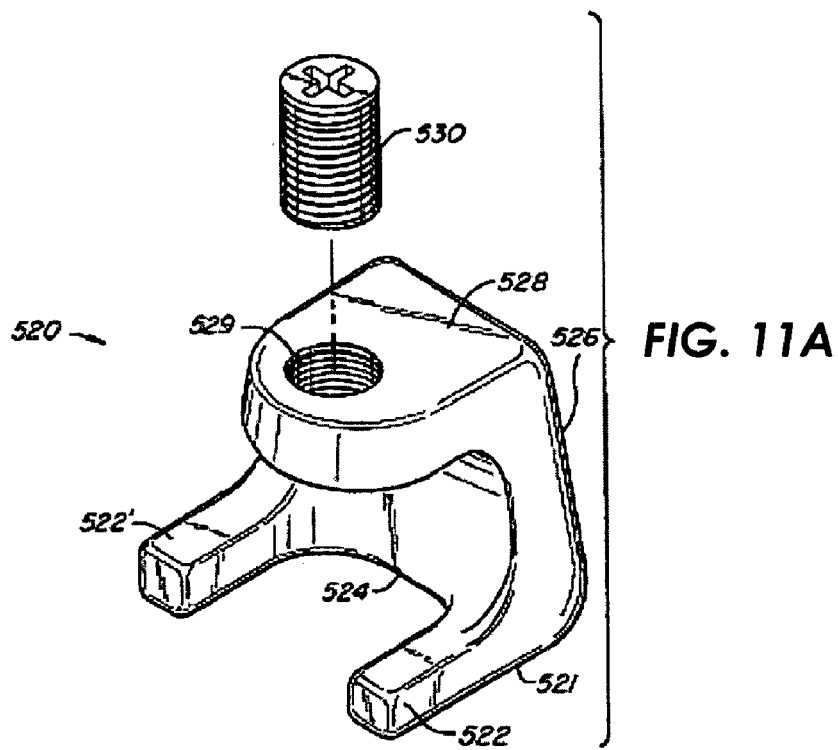
FIG. 11A illustrates a securing device for use in connection with an arthroplasty device to revise and/or modify, control, or limit motion of the arthroplasty device.

FIG. 11A illustrates a revision or securing device for use in connection with an arthroplasty device to revise and/or modify, control, or limit motion of the arthroplasty device. The securing device has a body 520 with a distal surface 521 having pair of prongs 522, 522'. When installed, the prongs 522, 522' form a base and are positioned below the crossbar member and the indenture 524 of the securing device engages the anchors on three sides. When used with a device of FIG. 1, the prongs can be positioned below the caudal cup which receives an end of the crossbar member, while the top sits above the crossbar end (110, 115) to secure the end in place within the caudal cup 150.

Figure 11B:
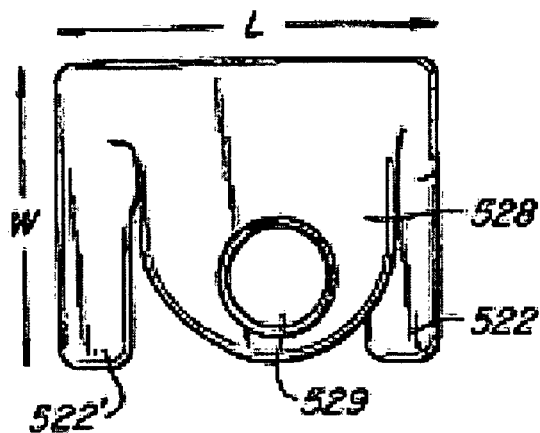
FIG. 11B is a top view of the securing device of FIG. 11A.
Figure 11C:
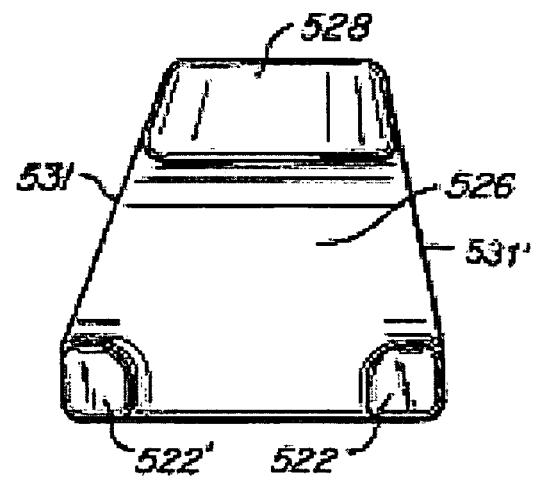
FIG. 11C is a side view of the securing device of FIG. 11A.
Figure 11D:
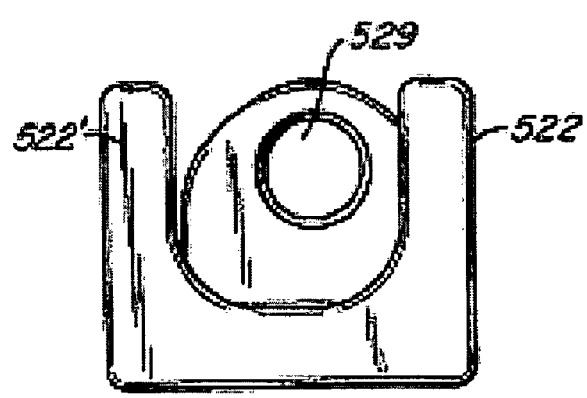
FIG. 11D is a bottom view of the securing device of FIG. 11A.
Figure 11E:
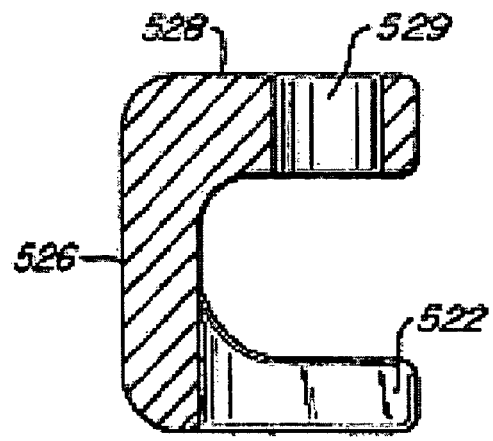
FIG. 11E is a cross-sectional view of the securing device of FIG. 11A.

The prongs 522, 522' engage a wall 526 of the securing device on one side. The wall 526 mates with a top or roof 528 that fits above the cross-bar member. The top 528 has an aperture 529. The aperture 529 can function as a detent, catch or plunger to snap fit over the ball end 110 of the crossbar member in an arthroplasty device. Alternatively, the securing device can be a securing mechanism, such as a set screw 530. FIG. 11B is a top view of the securing device 520. From this perspective, it is apparent that the top 528 can be positioned off a central axis of the device to the two prongs 522, 522', thus also potentially positioning the aperture 529 off the central axis as well. FIG. 11C is a side view of the securing device, illustrating the angled configurations of the sides 531, 531' back wall 526. The angled configuration positions the top 528, which can have a smaller dimension in at least one direction (e.g., length or width) than the length or width formed by the prongs and the wall. FIG. 11D is a bottom view of the securing device 520. FIG. 11E is a cross-sectional view of the securing device taken through an axis parallel to the prongs 522, 522'.

Figure 12A:
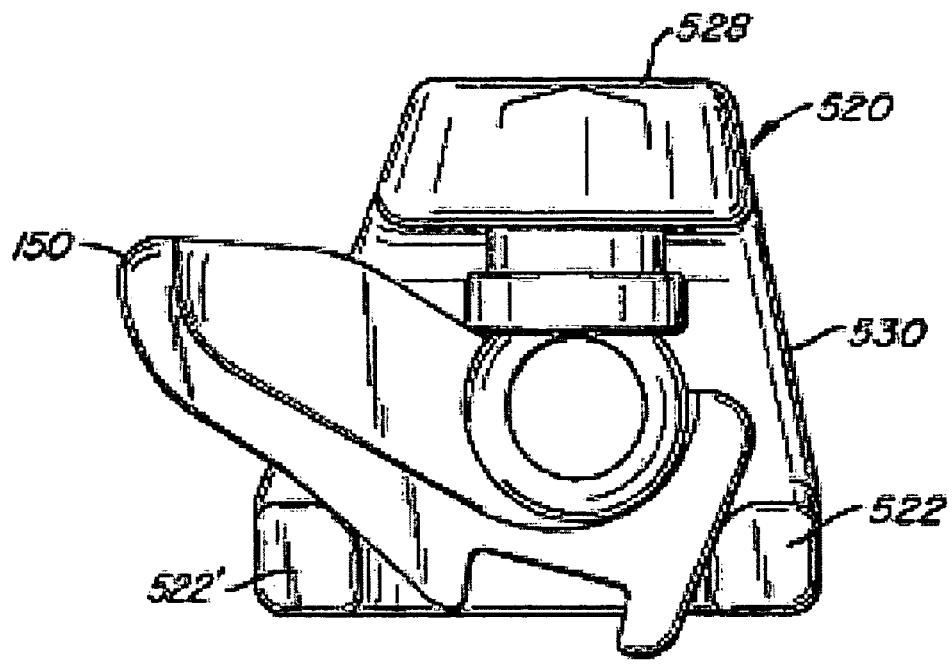
FIG. 12A illustrates a side view of the securing device of FIG. 11 in combination with a portion of the arthroplasty device of FIG. 1.
Figure 12B:
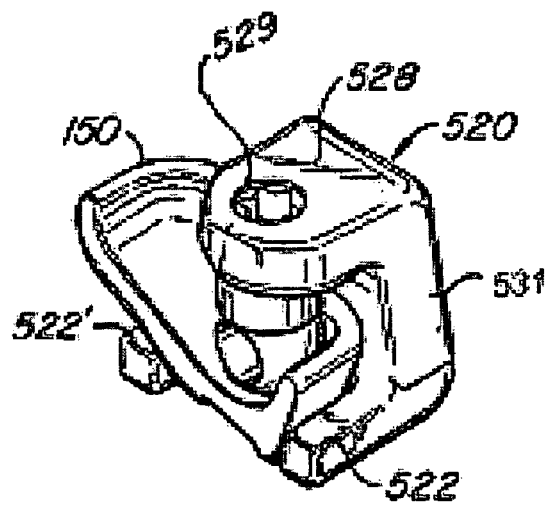
FIG. 12B illustrates a perspective view of the securing device in combination with a portion of the arthroplasty device.
Figure 12C:
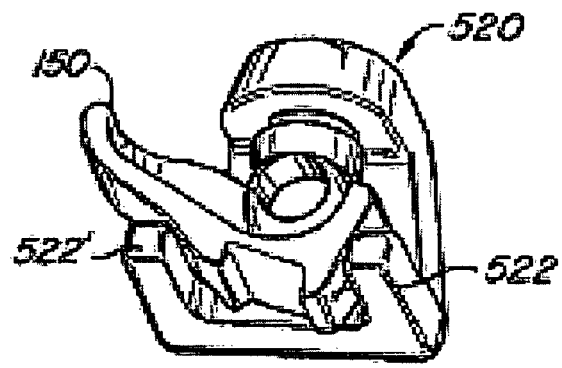
FIG. 12C is a perspective view from an anterior perspective of the securing device in combination with a portion of the arthroplasty device.
Figure 12D:
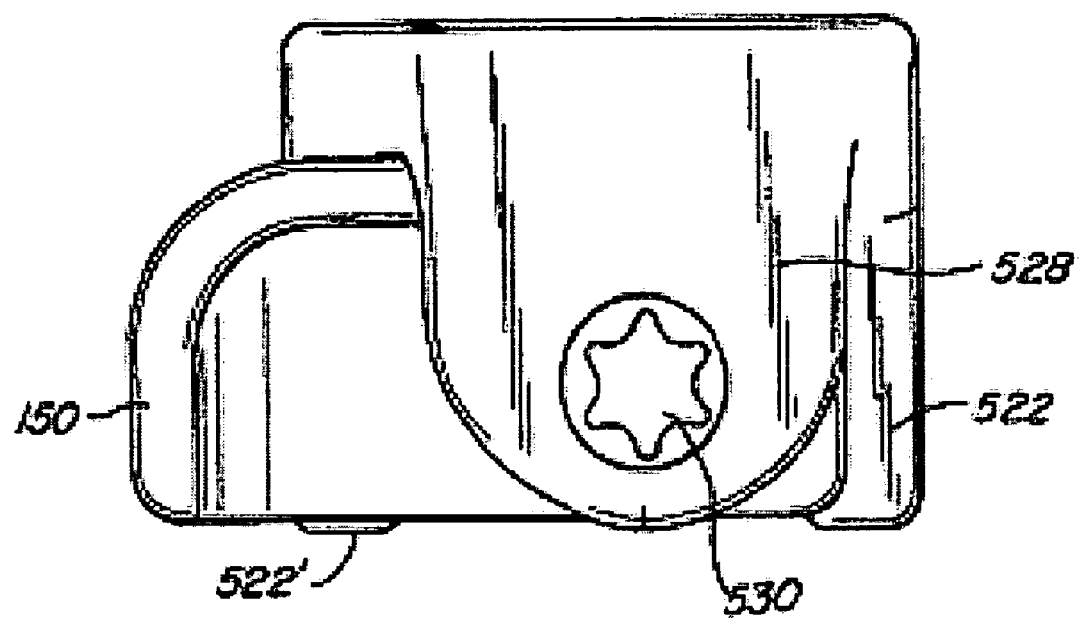
FIG. 12D is a top view of the securing device with a portion of the arthroplasty device
Figure 12E:
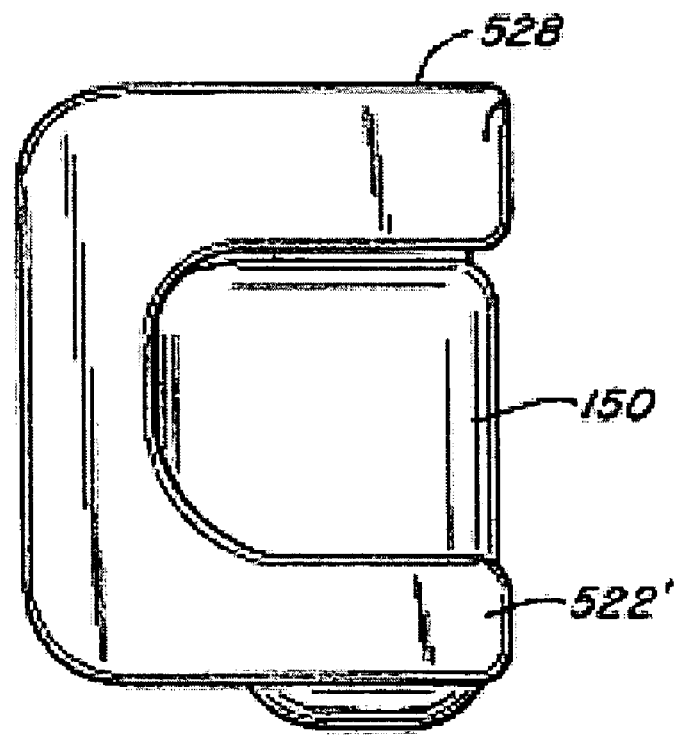
FIG. 12E is a bottom view of the securing device with a portion of the arthroplasty device.

FIG. 12A illustrates a side view of the securing device of FIG. 11 in combination with a portion of an arthroplasty device, such as the arthroplasty device of FIG. 1. The prongs 522, 522' sit below the caudal cup 150, holding the caudal cup in a fixed position. The top 528 of the securing device 520 sits above an end of the cross-member 110, which fits within the caudal cup 150. An anchoring device 530 (see FIG. 11A) can be fed through the aperture to engage the end of the cross-member and hold it in position within the caudal cup 150. As illustrated, the caudal cup 150 is tilted t toward an axial plane 52, enabling the caudal cup to secure the cross-member at a location. Adjustment of the position of the caudal cup relative to the cross-member end can affect the position of the device. FIG. 12B illustrates a perspective view of the securing device in combination with a portion of the arthroplasty device. From this perspective, a set screw 530 located within the aperture 529 on the top of the securing device can be seen. FIG. 12C is a perspective view from a partially anterior view of the securing device again in combination with a portion of the arthroplasty device. FIG. 12D is a top view of the securing device 520 with a portion of the arthroplasty device. As evident from this perspective, the caudal cup extends on one side past the prong 522'. The set screw 530 is positioned off-center relative to the length of the securing device, but the top of the securing device is positioned over the end of the cross-member. FIG. 12E is a bottom view of the securing device engaging an arthroplasty device. From this view, it is illustrated that the prongs 522, 522' are seated beneath, for example, the caudal cup of the arthroplasty device.

Thus, the implanted arthroplasty device can be revised to incorporate locks or "fusion caps" that desirably convert the device from an articulating joint replacement construct to a non-articulating (or controlled and/or limited articulation) spinal fusion construct. In this embodiment, the fusion cap can be installed on or into the caudal cups to desirably immobilize the cephalad bearings within the cups. In various embodiments, the fusion caps could immobilize the cephalad bearings by direct compression or contact, through use of a set screw or other device to secure the cephalad bearing relative to the cup, or the fusion cap could contain or cover an encapsulating material, such as bone cement, which could fill the caudal cup and immobilize the cephalad bearing. Various techniques could be used in conjunction with the installation of such fusion caps, and the cap could be installed prior to, during, or after the completion of a concurrent spinal fusion procedure, including the removal of intervertebral disc material, installation of fusion cages, and/or introduction of material (such as bone graft material) that desirably promotes spinal fusion. If desired, the bearing surface could be textured and/or knurled to increase friction between the ball, bearing surface and/or the fusion construct. Alternative embodiments could incorporate bearings of different shapes or sizes (not shown), including square or non-spherical bearings and/or bearings shaped to that fit snugly into and accommodate most or all of the interior of the caudal cup (not shown), that can be secured within the cup in a similar manner.

Figure 13A:
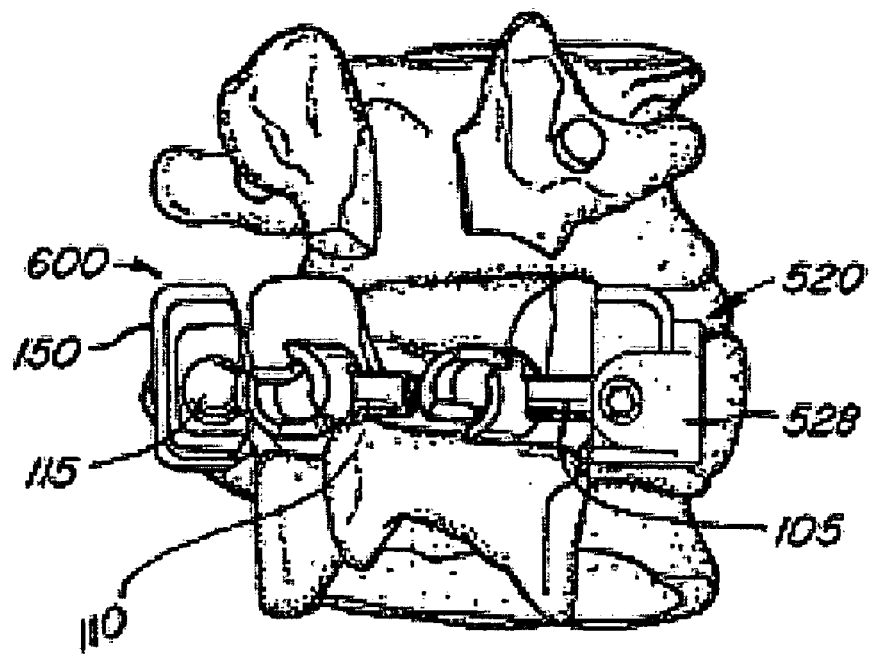
FIG. 13A is a perspective view of an implanted arthroplasty device with the securing device of FIG. 11.
Figure 13B:
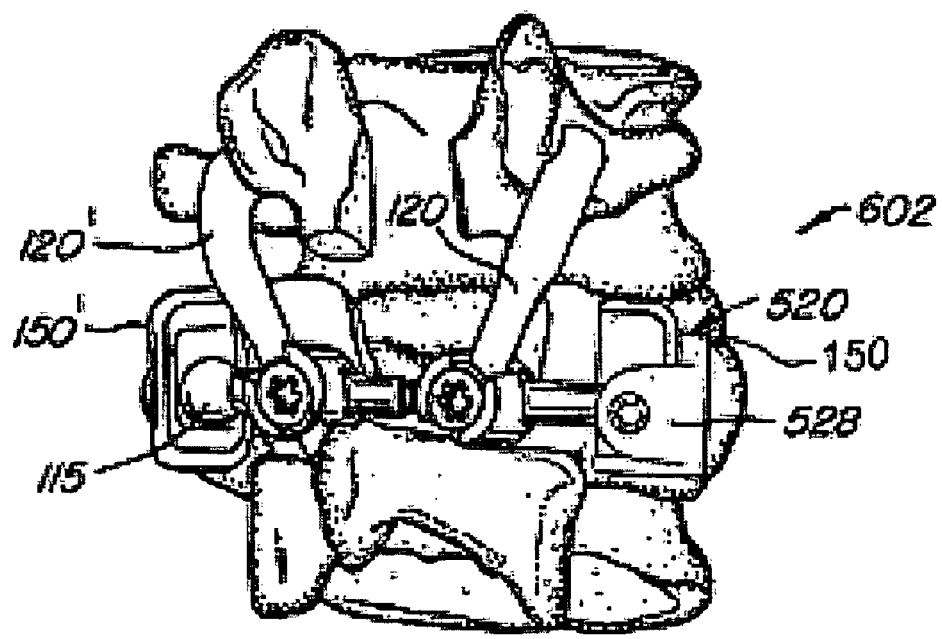
FIG. 13B is a perspective view of another implanted arthroplasty device with the securing device of FIG. 11.

Turning now to FIG. 13A, a perspective view of an implanted arthroplasty device 600 with the securing device of FIG. 11 is illustrated. The arthroplasty device 600 features a pair of caudal cups 150 engaging a cross-member 110. The cephalad arms have been removed, but it has been determined desirable to keep the caudal cups and cross-bar in place. The use of the securing device enables the caudal cup and crossbar member to be retained in position even without one or more of the cephalad arms to anchor the cross-member. Additionally, as will be appreciated by those of skill in the art, one of the two cephalad arms could be removed with the use of one or two of the securing devices to provide a three-point secured device (i.e., rigidly connecting two caudal cups to a single cephalad arm). The securing device engages the caudal cup and an end of the cross-member in the manner described above. FIG.

Figure 13C:
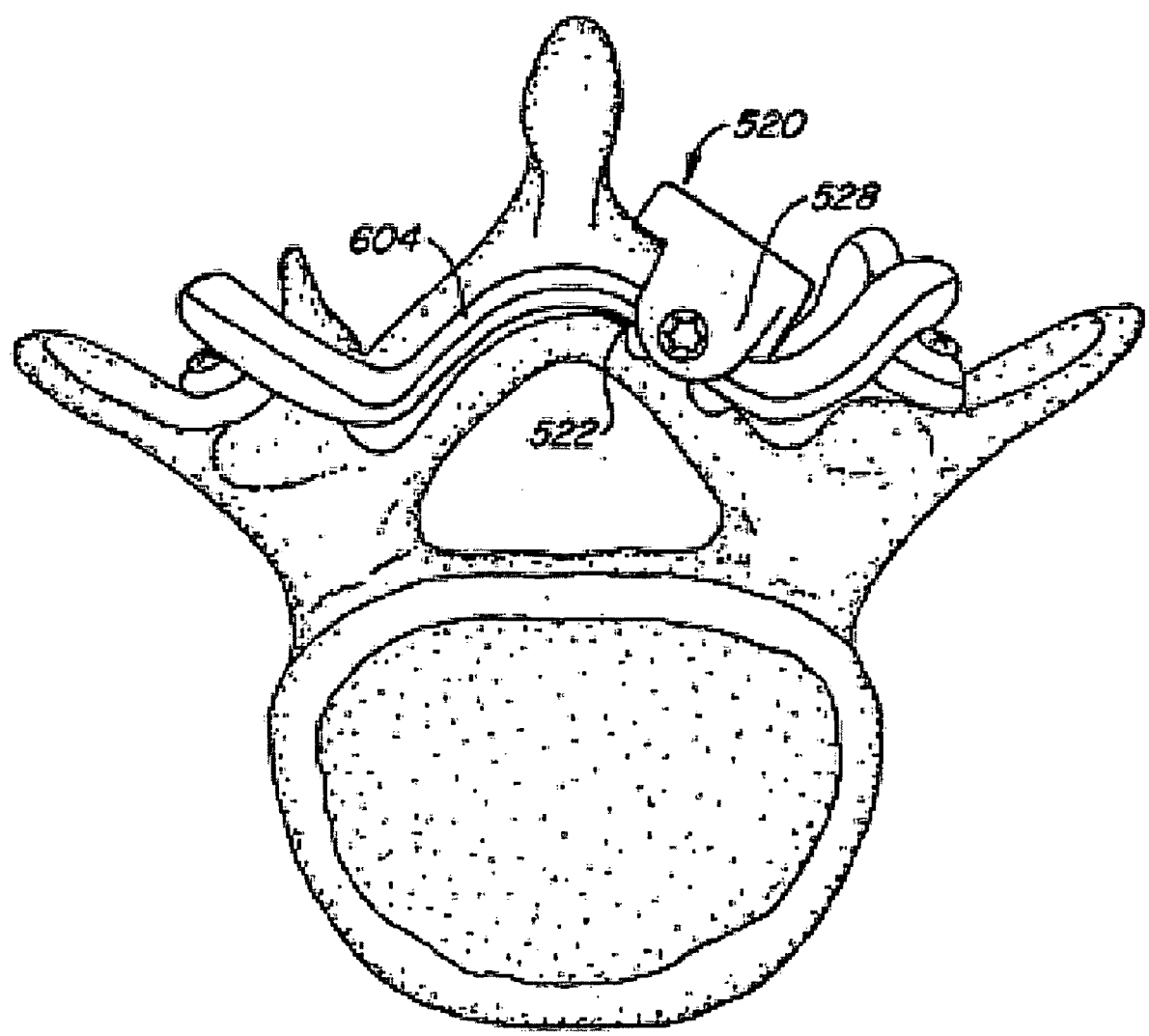
FIG. 13C is a perspective view of yet another implanted arthroplasty device with another embodiment of a securing device constructed in accordance with the teachings of the present invention.

13B is a perspective view of another implanted spinal arthroplasty device 602 having a pair of caudal cups 150, 150' engaging a cross-member 110 and a pair of cephalad arms 120, 120' extending vertically toward the adjacent vertebra 12 along with the securing device of FIG. 11. FIG. 13C is a perspective view of yet another implanted arthroplasty device 604 with the securing device of FIG. 11.

Figure 14:
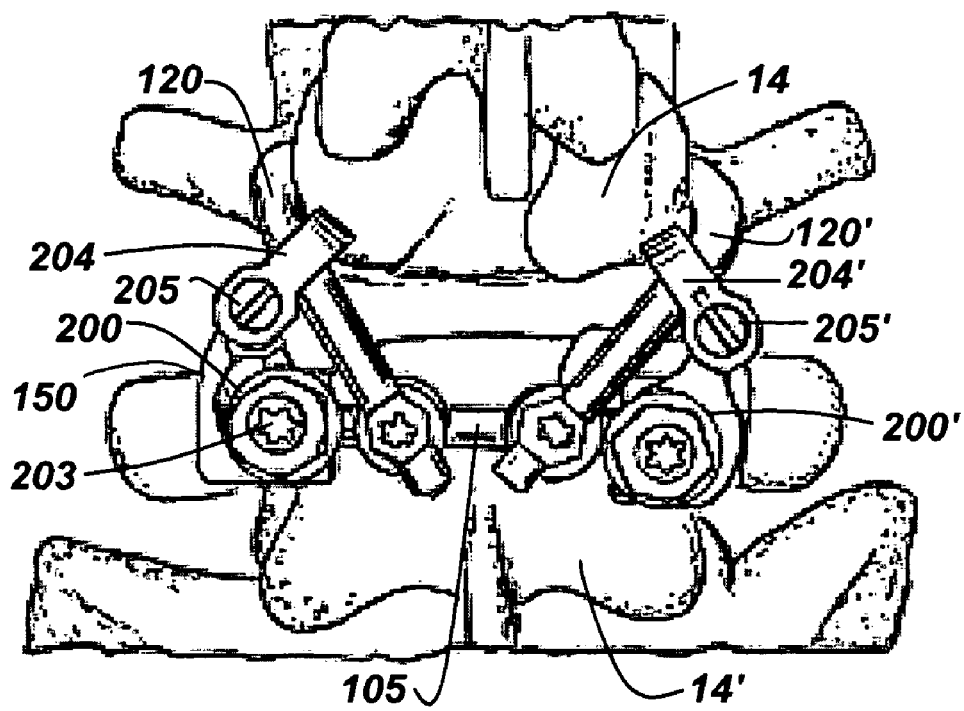
FIG. 14 shows an implanted spinal arthroplasty device that has been revised by a revision device according to another embodiment of the invention.
Figure 15:
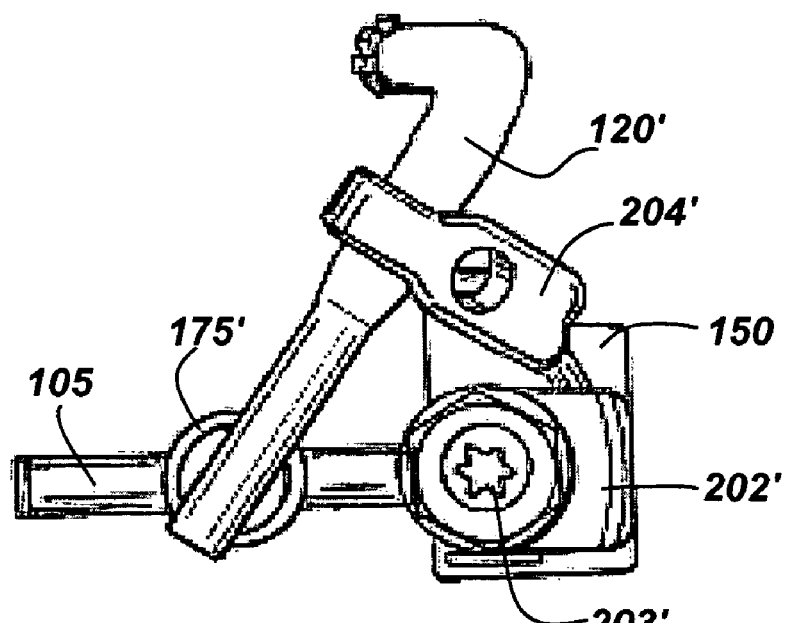
FIG. 15 shows a top view of certain components of the revision device and implanted arthroplasty device of FIG. 14.
Figure 16:
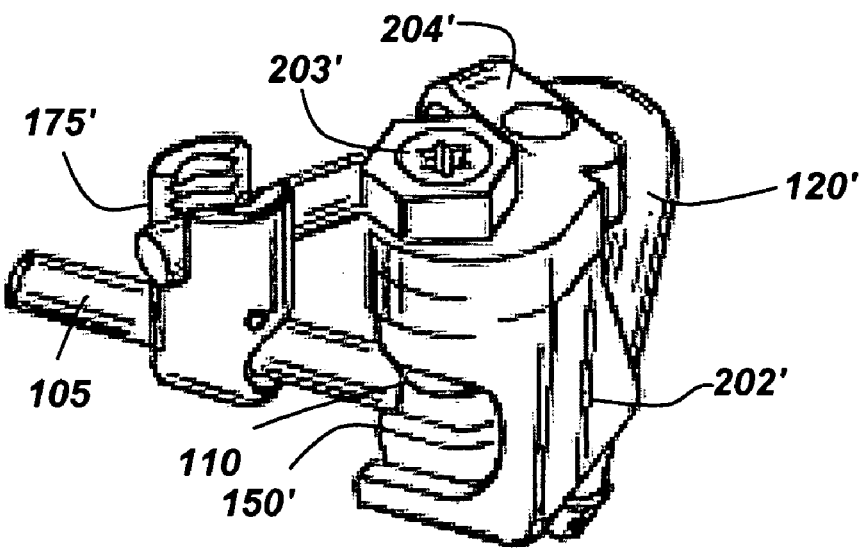
FIG. 16 shows a perspective view of certain components of the revision device and implanted arthroplasty device of FIG. 14.

FIGS. 14-18 show still other embodiments of a spinal arthroplasty revision system according to the invention. FIGS. 14-16 show an implanted spinal arthroplasty system (such as that shown in FIG. 1) with cephalad arms 120 and 120', cephalad heads (such as head 110 shown in FIG. 16) at either end of a cephalad crossbar 105 and caudal cups 150 and 150'. The cephalad arms connect to crossbar 105 via crossbar mounts 175 and 175'. Revision devices 200 and 200' have been added to the implanted arthroplasty prosthesis to substantially eliminate movement between the cephalad heads and the caudal cups and, thereby, between adjacent vertebrae 14 and 14'. As shown in detail in FIGS. 15 and 16, the revision device includes a securing section 202' similar to that of FIG. 11 extending from one side of the caudal cup 150' to an opposing side of the cephalad head 110. Securing sections 202 and 202' lock the cephalad heads against the caudal cups with screws and 203 and 203'. Cephalad arm hook plates and connectors 204 and 204' are attached to the securing section 202' (via screw 203 or 203') and to cephalad arms 120 and 120' (via set screw 205 or 205') to provide additional stability. The upper surfaces of the securing sections 202 and 202's and the lower surfaces of hook plates 204 and 204' may have complementary shapes (e.g., spherical) and roughened surface texture to form a more secure connection between them. Revision devices 200 and 200' alter the biomechanics of the implanted device by substantially eliminating movement between the cephalad and caudal members and between the adjacent vertebrae, thereby transforming the implanted spinal arthroplasty device into a fusion device.

Figure 17:
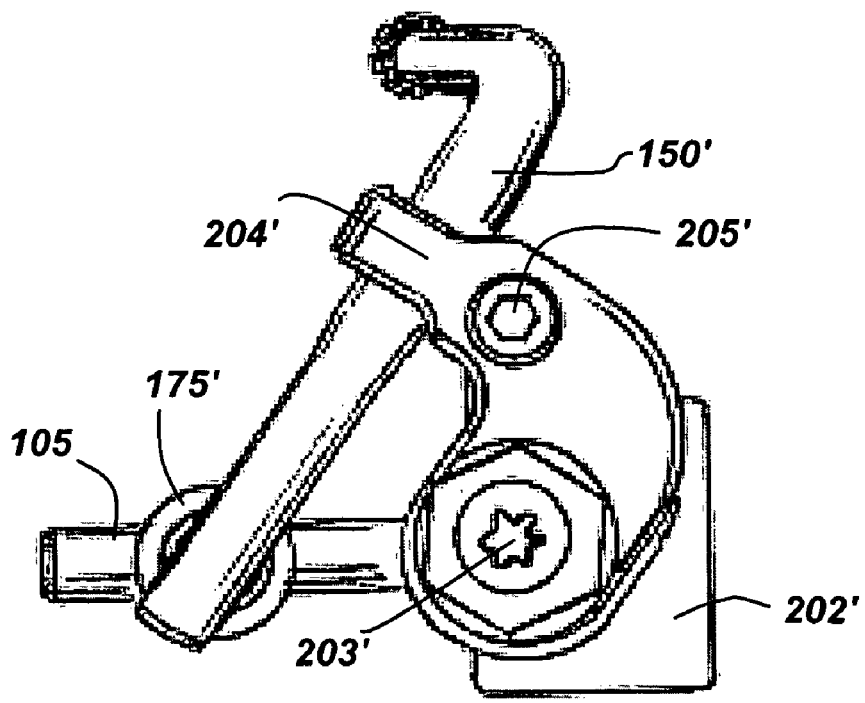
FIG. 17 shows a top view of certain components of an alternative revision device and implanted arthroplasty device.
Figure 18:
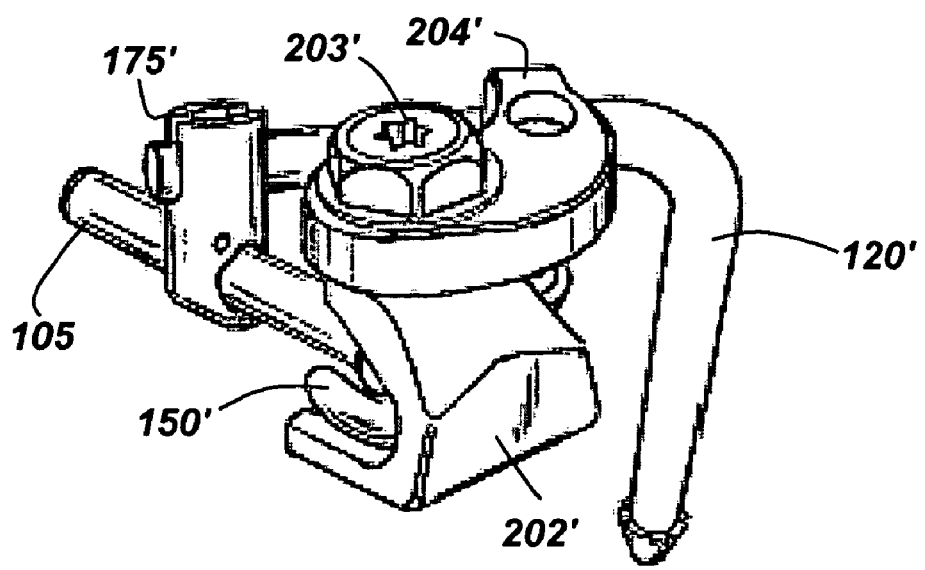
FIG. 18 shows a perspective view of the components of the revision device and implanted arthroplasty device of FIG. 17.

FIGS. 17 and 18 show an alternative design to the revision devices 200 or 200' of FIGS. 14-16.

The first step of adding a revision system, such as one of those shown above in FIGS. 14-18, to an implanted spinal arthroplasty device, is to expose the existing device. Bone and/or soft tissue may be removed from under the caudal cup to make room for the securing device, such as securing device 202 or 202' in FIGS. 14-18. After placing the securing devices 202 and 202' around caudal cups 150 and 150' and the cephalad heads at either end of crossbar 105, screws 203 and 203' are tightened (to, e.g., 70 in-lbf) to hold the cephalad and caudal components together. The cephalad heads are preferably in the "home" position within their respective caudal cups. The vertebrae can be compressed prior to final assembly of the revision device, if desired. A hook plate of suitable size and dimensions is selected (from, e.g., a kit containing multiple hook plates of various sizes) and placed over a portion of the securing device screw 203 or 203' extending above the securing device 202 or 202'. The hook plate is attached to its corresponding cephalad arm via set screw 205 or 205'. Bone graft material may be added to facilitate fusion. The incision may then be irrigated and closed in a standard fashion.

The revision devices of this invention may be provided in kits containing components of various sizes so that the revision device can be tailored to the patient's anatomy. In addition, the kits may contain the removal, sizing and implantation tools needed to perform the revision procedure.

Figure 19:
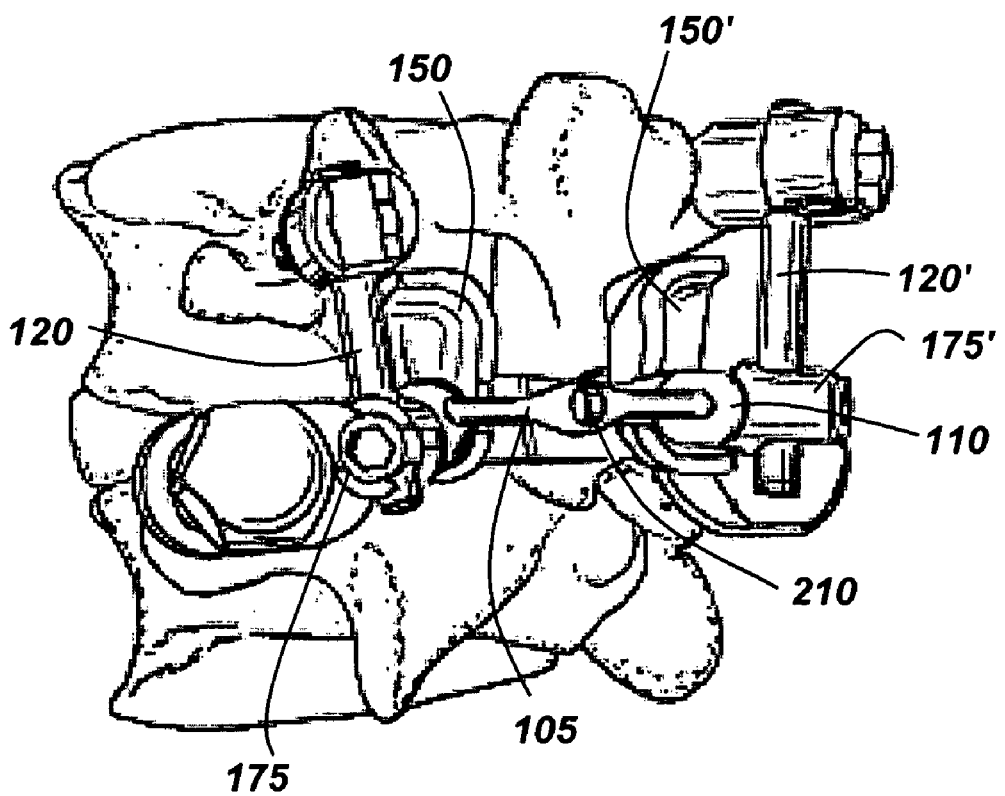
FIG. 19 shows an implanted spinal arthroplasty device with attachment holes for a revision device.

FIG. 19 shows an implanted spinal arthroplasty device similar to that shown in FIG. 1. As in the FIG. 1 embodiment, cephalad arms 120 and 120' connect via crossbar mounts 175 and 175' to a cephalad crossbar 105 having heads 110 and 115 at either end. In this device, however, the caudal cups 150 and 150' are connected with a crossbar 212 as well. In addition, cephalad crossbar 105 has an opening 210 that lines up with an opening (not shown) in caudal crossbar 212. The two openings may be used to secure a revision device, e.g., to secure the cephalad and caudal components together during installation or to limit or eliminate the range of motion between the cephalad and caudal components.

While the various embodiments of the invention have been described in the context of a spinal arthroplasty device revision that substantially eliminates motion between the cephalad and caudal device components (i.e., fusion), it should be understood that the revision device may alter but still permit motion between the cephalad and caudal components.

What is claimed is:

1. A method of revising an implanted arthroplasty device, the implanted arthroplasty device comprising a cephalad component fixed to a first vertebra and a caudal component fixed to a second vertebra inferior to the first vertebra, the method comprising: removing a portion of a previously implanted spinal arthroplasty device; and attaching a revision component to a remaining portion of the previously implanted spinal arthroplasty device to alter a biomechanical characteristic of the implanted arthroplasty device.

2. The method of claim 1 wherein the caudal component comprises a caudal cup, the removing step comprising removing the caudal cup from a fixation element.

3. The method of claim 2 wherein the attaching step comprises attaching an attachment device to the caudal cup fixation element.

4. The method of claim 1 wherein the cephalad component comprises a cephalad arm and a cephalad bearing element, the removing step comprising removing the cephalad bearing element from the cephalad arm.

5. The method of claim 4 wherein the attaching step comprises attaching a connector housing to the cephalad arm and attaching the connector housing to an other arthroplasty element or revision component.

6. The method of claim 5 wherein the caudal component comprises the other arthroplasty element.

7. The method of claim 5 wherein the removing step further comprises removing a caudal cup from a caudal fixation element, the attaching step comprising attaching a caudal attachment device to the caudal fixation element and attaching the housing to the caudal attachment device.

8. The method of claim 4 wherein the cephalad component comprises two cephalad arms, the attaching step comprising attaching a crossbar to the two cephalad arms.

9. The method of claim 1 wherein the cephalad component comprises an implanted cephalad arm, the removing step comprising removing a portion of the implanted cephalad arm.

10. The method of claim 9 wherein the attaching step comprises attaching a new cephalad arm to a remaining portion of the implanted cephalad arm.

11. The method of claim 10 wherein the attaching step comprises attaching a connector housing to the new cephalad arm and attaching the connector housing to an other arthroplasty element or a revision component.

12. The method of claim 11 wherein the caudal component comprises the other arthroplasty element.

13. The method of claim 11 wherein the removing step further comprises removing a caudal cup from a caudal fixation element, attaching step comprises attaching a caudal attachment device to the caudal fixation element and attaching the housing to the caudal attachment device.

14. The method of claim 10 wherein the cephalad component comprises two implanted cephalad arms, the removing step comprising removing a portion of each implanted cephalad arm, the attaching step comprising attaching a new cephalad arm to a remaining portion of each implanted cephalad arm and attaching a crossbar to the two new cephalad arms.

15. The method of claim 10 wherein attaching a new cephalad arm comprises attaching a new cephalad arm medial to the implanted cephalad arm.

16. The method of claim 10 wherein attaching a new cephalad arm comprises attaching a new cephalad arm lateral to the implanted cephalad arm.

17. A method of altering the biomechanics between first and second vertebrae comprising: accessing an implanted spinal device comprising a cephalad component fixed to the first vertebra and a caudal component fixed to the second vertebra inferior to the first vertebra, the cephalad and caudal components having a biomechanical relationship between them, and attaching a revision component to the cephalad and caudal components to alter the biomechanical relationship.

18. The method of claim 17 wherein the implanted spinal device comprises a spinal arthroplasty device.

19. The method of claim 17 wherein the implanted spinal device comprises a facet joint replacement device.

20. The method of claim 17 wherein the implanted spinal device comprises a dynamic stabilization device.

21. The method of claim 17 wherein the implanted spinal device comprises an interspinous spacer.

22. The method of claim 17 wherein the implanted spinal device comprises an artificial disc.

23. The method of claim 17 wherein the biomechanical relationship is a range of motion between the cephalad and caudal components, the attaching step comprising attaching a revision component to the cephalad and caudal components to alter the range of motion.

24. The method of claim 23 wherein the attaching step comprises substantially eliminating motion between the cephalad and caudal components.

25. The method of claim 17 wherein the cephalad component comprises a cephalad bearing element and the caudal component comprises a caudal bearing element, the attaching step comprising attaching a revision component extending from one side of the cephalad bearing element to an opposing side of the caudal bearing element.

26. The method of claim 25 wherein the cephalad component further comprises a cephalad arm, attaching step further comprising attaching the revision component to the cephalad arm.

27. A revision device for an implanted spinal arthroplasty device, the implanted spinal arthroplasty device comprising a cephalad component fixed to a first vertebra and a caudal component fixed to a second vertebra inferior to the first vertebra, the revision device comprising an attachment component adapted to attach to a remaining portion of an arthroplasty device component after a portion of the arthroplasty device has been removed to alter a biomechanical characteristic of the arthroplasty device.

28. The revision device of claim 27 wherein the caudal component comprises a caudal cup, the revision device comprises a caudal attachment device adapted to be attached to a caudal cup fixation element after the caudal cup has been removed.

29. The revision device of claim 27 wherein the cephalad component comprises a cephalad arm, revision device comprises a connector housing adapted to be attached to the cephalad arm and to an other arthroplasty element or a revision component.

30. The revision device of claim 29 wherein the caudal component comprises the other arthroplasty element.

31. The revision device of claim 29 further comprising a caudal attachment device adapted to be attached to a caudal cup fixation element after the caudal cup has been removed, the connector housing being adapted to be attached to the caudal attachment device.

32. The revision device of claim 27 further comprising a cross-bar adapted to attach to two cephalad arms of the implanted spinal arthroplasty device.

33. The revision device of claim 27 wherein the implanted spinal arthroplasty device comprises a cephalad arm, the revision device further comprises a new cephalad arm and an attachment mechanism adapted to attach the new cephalad arm to a remaining portion of the implanted cephalad arm after a portion of the implanted cephalad arm has been removed.

34. The revision device of claim 33 further comprising a connector housing attached to the new cephalad arm and being adapted to attach to an other arthroplasty device element or revision device element.

35. The revision device of claim 34 wherein the caudal component comprises the other arthroplasty element.

36. The revision device of claim 34 further comprising a caudal attachment device adapted to be attached to a caudal cup fixation element after the caudal cup has been removed, the connector housing being adapted to be attached to the caudal attachment device.

37. The revision device of claim 33 wherein the implanted spinal arthroplasty device comprises two cephalad arms, the revision device comprising two new cephalad arms, each having an attachment mechanism adapted to attach one of the new cephalad arms to a remaining portion of a respective implanted cephalad arm after a portion of such implanted cephalad arm has been removed.

38. The revision device of claim 33 wherein the attachment mechanism is adapted to attach the new cephalad arm medial to the implanted cephalad arm.

39. The revision device of claim 33 wherein the attachment mechanism is adapted to attach the new cephalad arm lateral to the implanted cephalad arm.

* * * * *